United States Patent
Zhang et al.

(10) Patent No.: US 11,485,696 B2
(45) Date of Patent: Nov. 1, 2022

(54) MANUFACTURING METHOD FOR HIGH-PURITY CYCLOHEXENONE LONG-CHAIN ALCOHOL

(71) Applicant: TAIHO PHARMACEUTICAL CO., LTD., Tokyo (JP)

(72) Inventors: Jian Zhang, Shanghai (CN); Dehui Jiang, Shanghai (CN); Xiaojun Shen, Shanghai (CN)

(73) Assignee: Taiho Pharmaceutical Co., Ltd., Tokyo (JP)

( * ) Notice: Subject to any disclaimer, the term of this patent is extended or adjusted under 35 U.S.C. 154(b) by 865 days.

(21) Appl. No.: 16/071,709

(22) PCT Filed: Jan. 22, 2017

(86) PCT No.: PCT/CN2017/072078
§ 371 (c)(1),
(2) Date: Jul. 20, 2018

(87) PCT Pub. No.: WO2017/125087
PCT Pub. Date: Jul. 27, 2017

(65) Prior Publication Data
US 2021/0101859 A1    Apr. 8, 2021

(30) Foreign Application Priority Data
Jan. 22, 2016 (CN) .......................... 2016-10044990.8

(51) Int. Cl.
| C07C 45/51 | (2006.01) |
| C07C 45/42 | (2006.01) |
| C07C 249/16 | (2006.01) |
| C07C 49/713 | (2006.01) |
| C07C 49/753 | (2006.01) |
| C07C 251/84 | (2006.01) |

(52) U.S. Cl.
CPC ............ *C07C 45/516* (2013.01); *C07C 45/42* (2013.01); *C07C 249/16* (2013.01); *C07C 49/713* (2013.01); *C07C 49/753* (2013.01); *C07C 251/84* (2013.01)

(58) Field of Classification Search
CPC ..... C07C 45/516; C07C 45/42; C07C 249/16; C07C 49/713; C07C 49/753; C07C 251/84; C07C 45/45; C07C 45/64; C07C 281/14; C07C 311/49; C07C 251/86
USPC .................................................. 568/343
See application file for complete search history.

(56) References Cited

U.S. PATENT DOCUMENTS

| 3,912,779 A | 10/1975 | Tarnow et al. |
| 2004/0115810 A1 | 6/2004 | Luu et al. |
| 2012/0071696 A1 | 3/2012 | Griesbach et al. |

FOREIGN PATENT DOCUMENTS

| JP | S4743521 B | 11/1972 |
| JP | S49110835 A | 10/1974 |
| JP | H1017520 A | 1/1998 |
| JP | 2001515058 A | 9/2001 |
| JP | 200381979 A | 3/2003 |
| JP | 2003-212811 A | 7/2003 |
| JP | 201151904 A | 3/2011 |
| JP | 2013538220 A | 10/2013 |
| WO | 9908987 A1 | 2/1999 |
| WO | 02/066023 A1 | 8/2002 |
| WO | 2004/087630 A1 | 10/2004 |
| WO | 2013147072 A1 | 10/2013 |

OTHER PUBLICATIONS

Greene, Protective Groups in Organic Synthesis, 1999, 3rd Ed., pp. 350-358.
Greene, Protective Groups in Organic Synthesis, 1999, 3rd Ed., pp. 27-54.
Notification of Reason for Refusal cited in the Office Action dated Mar. 16, 2021 for the corresponding KR patent application No. 10-2018-7023680, 23 pages.
Luu et al., "Cyclohexenonic Long-Chain Fatty Alcohols as Neuronal Growth Stimulators", Molecules, 2000, vol. 5, pp. 1439-1460.
Girlanda-Junges et al., "3-(15-Hydroxypentadecyl)-2,4,4-trimethyl-2-cyclohexen-1-one and its Effect on Neuropeptide Secretion", Bioorganic & Medicinal Chemistry Letters, 2000, vol. 10, pp. 2537-2539.
Huber et al., "Experimental Studies on the Selective B—C—H Halogenation of Enones", The Journal of Organic Chemistry, 2015, vol. 80, No. 4, pp. 2281-2294.
Shirini et al., "Effective oxidative cleavage of C=N using chromium trioxide supported on NaHSO4H2O", Arkivoc, 2007, (i), pp. 34-39.
Levine et al., "Catalytic Enantioselective Approach to the Eudesmane Sesquiterpenoids: Total Synthesis of (+)-Carissone", Organic Letters, 2009, vol. 11, No. 2, 45 pages.
Lumb et al., "A Simple, mild and environmentally benign procedure for the cleavage of carbon-nitrogen double bonds using NaBrO3 in the presence of [bmim]HSO4", RSC Advances, 2014, vol. 4, pp. 47677-47689.
Kim et al., "Vinylogous Intramolecular Nucleophilic Acyl Substitution Reactions Mediated by Samarium (II) Iodide", Bulletin of the Korean Chemical Society, 2000, vol. 21, No. 12, pp. 1175-1176.

(Continued)

*Primary Examiner* — Ana Z Muresan
(74) *Attorney, Agent, or Firm* — Rothwell, Figg, Ernst & Manbeck, P.C.

(57) ABSTRACT

This invention relates to a method for producing a high-purity cyclohexenone long-chain alcohol represented by formula I, and produces the compound of formula I by a metal-mediated Barbier reaction. The method of the present invention has advantages in its short scheme, high yield, and high-purity product, and is suitable for industrial scale up.

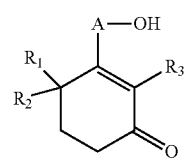

I

15 Claims, No Drawings

(56) References Cited

OTHER PUBLICATIONS

Murugan et al., "Solvent Free Rapid Synthesis of 3-Alkoxycyclohex-2-en-1-one from 1,3-Cyclohexanedione Promoted by Indium (III) Chloride/Silica Gel", Australian Journal of Chemistry, 2005, vol. 58, No. 3, pp. 228-230.
Office Action for TW patent application No. 106102506 dated Aug. 25, 2020, 8 pages.
McMurry, "19.11 Nucleophilic Addition of Hydride: Reduction", Organic Chemistry, vol. 2, 4th edition, 1998, pp. 740-745.
Takeshi Oishi, "Protective Group in Organic Synthesis, Protecion of Hydroxyl Group", Organic synthesis chemistry, 1978, vol. 36, No. 9, pp. 715-722.
Peter G. M. Wuts, Greene's protective groups in organic synthesis, 5th edition, 2014, pp. 33-43.
Notice of Reasons for Refusal cited in Japanese Patent Application No. 2018-538103, dated Jul. 16, 2019, 7 pages.
Ushakov, "Studies towards the synthesis of crotogoudin", SYNLETT, 2013, 24(6), pp. 705-708.
Office action dated Sep. 28, 2021 for CN Pat. Appln. No. 201610077424.7, 15 pages.

MANUFACTURING METHOD FOR HIGH-PURITY CYCLOHEXENONE LONG-CHAIN ALCOHOL

CROSS REFERENCE TO RELATED APPLICATION

This application is a 35 U.S.C. 371 National Phase Entry Application from PCT/CN2017/072078 filed Jan. 22, 2017, which claims priority to Chinese Application No. 2016-10044990.8, filed on Jan. 22, 2016, the disclosures of which are incorporated herein in their entirety by reference, and priority is claimed to each of the foregoing.

TECHNICAL FIELD

The present invention pertains to the fields of pharmacochemistry and synthetic chemistry, and specifically relates to a method for producing a high-purity cyclohexenone long-chain alcohol.

BACKGROUND ART

Nerves growth factor (NGF) is present primarily in the hippocampus and the area of the cerebral cortex, playing a role in the regulation of survival, growth and development, differentiation, regeneration, and functional maintenance of neurons. NGF acts not, only on catecholaminergic neurons in the peripheral nervous system, but also on cholinergic neurons in the brain. Alzheimer's disease is believed to be associated with degeneration and loss of cholinergic neurons. Researchers once attempted to treat. Alzheimer's disease by administering NGFs into the brain, but this type of therapeutic approach was unfit for humans because NGF is a macromolecular protein with a molecular weight of as high as 12000, which is unable to permeate the blood-brain barrier. Thus, researchers have devoted continuous effort to search for an NGF-like substance that can penetrate through the blood-brain barrier or a small-molecule compound that can stimulate NGF synthesis in the brain, and the use of such substances in the treatment of Alzheimer's disease. Long-chain aliphatic alcohols, such as cyclohexenone long-chain alcohols, are classified as small molecules that have a similar nature to that of NGF, and can stimulate the growth of neurons in the brain, showing promise in clinical application.

Literature, Molecules (2000, 5, 1439 to 1460), reports a method for producing a cyclohexenone long-chain alcohol as shown in scheme 1.

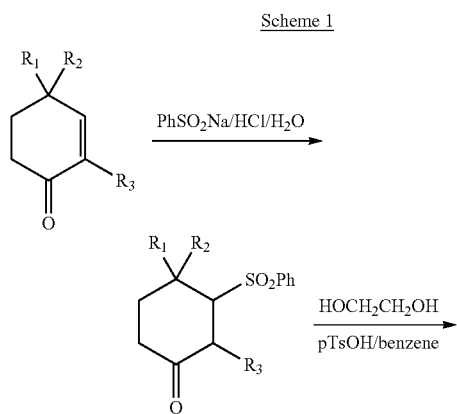

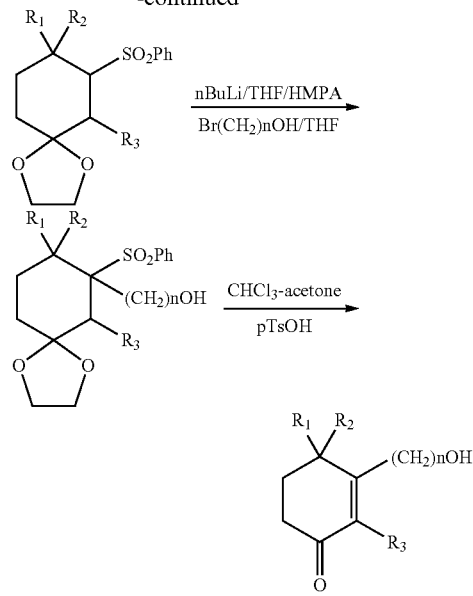

This method is disadvantageous in industrial production because unsaturated cyclohexanone, which is a starting material in scheme 1, is difficult to prepare; the total yield percentage of the method is low; the method uses butyl-lithium as a transmetalation reagent; and multiple type I solvents (which refer to human carcinogens and organic solvents suspected as human carcinogens or environmentally damaging substances) are involved in the scheme.

Literature, Bioorganic & Medicinal Chemistry Letters (2000, 10, 2537 to 2539), reports a production method shown in scheme 2.

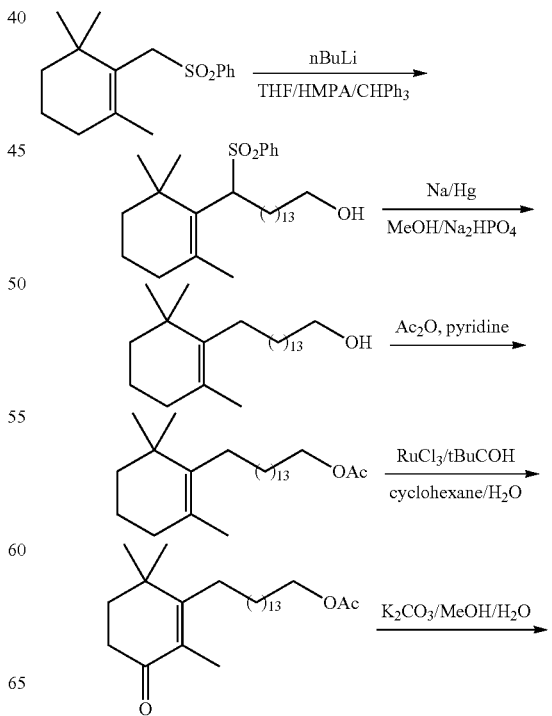

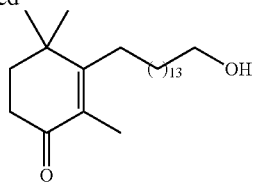

This method is disadvantageous in industrial production because sulfone, which is a starting material in scheme 2, is difficult to prepare; when the sulfone group is removed, highly toxic Na (Hg) needs to be used; and when the carbonyl group is introduced, ruthenium, a very expensive metal, and tert-butyl hydroperoxide, a highly hazardous substance, are used.

WO2004/087630 reports a production method shown in scheme 3.

Scheme 3

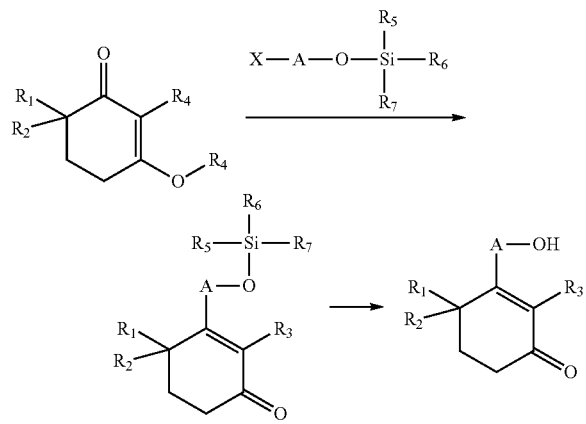

Scheme 3 uses a Grignard reagent to perform a 1,2-addition reaction with an unsaturated ketone. However, the productivity in the addition reaction is merely about 30%, and a large amount of halogenated hydrocarbon protected by silyl ether decomposes during the preparation of the Grignard reagent, considerably increasing the production cost. Additionally, the low productivity and the large amount of by-products generated in the preparation of the Grignard reagent make it extremely difficult to purify the product. Thus, this scheme is also not suitable for industrial production.

Moreover, preparation of a high-purity starting material drug is a major requirement in the development of a cyclohexenone long-chain alcohol as a medicinal substance and its clinical application. Cyclohexenone long-chain alcohols have a low melting point, and transform into an oil as the room temperature increases, which makes it difficult to purify them. Cyclohexenone long-chain alcohols reported in the literature above are all prepared into high-purity products by treatment with column chromatography. Since column chromatography is not suitable for industrial production because of the high cost and great loss, there has been a desperate need for a production method for a high-purity cyclohexenone long-chain alcohol that is produced in a short scheme at a high yield, easy to handle, and suitable for industrial production.

SUMMARY OF INVENTION

An object of the present invention is to provide a method for producing a high-purity cyclohexenone long-chain alcohol represented by formula I, and the method is achieved by the following reaction scheme:

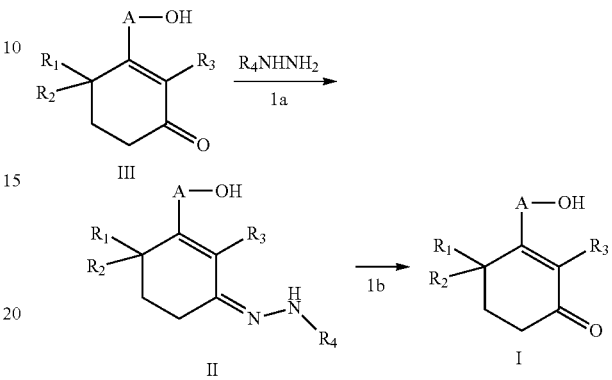

wherein
A represents $C_{10-18}$ alkylene,
$R_1$, $R_2$, and $R_3$ each independently represent H or methyl,
$R_4$ represents H, substituted or unsubstituted $C_{1-7}$ alkyl, substituted or unsubstituted $C_{6-14}$ aryl,

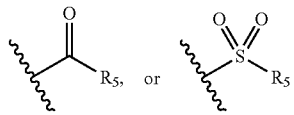

wherein the "substituted" means substituted with one substituent or two or more substituents selected from methyl, nitro, chlorine, and bromine; $R_5$ represents H, methoxy, tert-butoxy, benzyloxy, phenyl, 4-methylphenyl, or amino; and $R_4$ is preferably

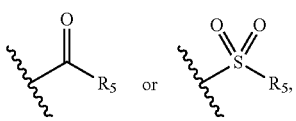

the method comprising the steps of
(1a) subjecting a cyclohexenone long-chain alcohol crude product product III and hydrazine or its derivative $R_4NHNH_2$ to a condensation reaction under suitable conditions to obtain a compound II, and
(1b) hydrolyzing the compound II in the presence of an acidic substance to obtain a high-purity cyclohexenone long-chain alcohol (compound I).

In this method, the high-purity cyclohexenone long-chain alcohol (compound I) has a purity by HPLC of more than 95%; preferably, the high-purity cyclohexenone long-chain alcohol has a purity by HPLC of more than 99%; and more preferably, the high-purity cyclohexenone long-chain alcohol has a purity by HPLC of more than 99.9%.

In this method, the suitable conditions stated in step (1a) means conditions under which an acid, an alkali, or a desiccant is present. The alkali is one member or two or more members selected from sodium alkoxide, potassium alkoxide, magnesium oxide, calcium oxide, sodium carbonate, potassium carbonate, lithium, carbonate, cesium carbonate, calcium carbonate, sodium acetate, potassium acetate, lithium acetate, sodium benzoate, potassium, benzoate, lithium, benzoate, triethylamine, trimethylamine, diisopropylethylamine, 1,8-diazabicyclo[5.4.0]undec-7-ene, 1,5-diazabicyclo[4.3.0]non-5-ene, and triethylenediamine, and preferably one member or two or more members selected from, sodium tert-butoxide, potassium tert-butoxide, sodium carbonate, potassium carbonate, sodium acetate, potassium acetate, triethylamine, and diisopropylethylamine. The acid is one member or two or more members selected from acetic acid, benzoic acid, hydrochloric acid, sulfuric acid, phosphoric acid, benzenesulfonic acid, p-toluenesulfonic acid, camphorsulfonic acid, boron trifluoride ethyl ether, indium trifluoromethanesulfonate, indium trifluoromethanesulfonate, and bismuth trifluoromethanesulfonate, and preferably one member or two or more members selected from acetic acid, p-toluenesulfonic acid, boron trifluoride ethyl ether, and bismuth trifluoromethanesulfonate. The desiccant is one member or two or more members selected from desiccants, such as a molecular sieve, magnesium sulfate, sodium sulfate, and calcium hydride, and preferably one member or two or more members selected from a molecular sieve and magnesium sulfate.

The molar ratio of the hydrazine or its derivative $R_4NHNH_2$ to the cyclohexenone long-chain alcohol crude product III is 0.8:1 to 3:1, and preferably 0.9:1 to 2:1. The condensation reaction is performed in a solvent, and the solvent is one member or two or more members selected from methanol, ethanol, isopropanol, n-butanol, tert-butanol, tert-pentanol, acetonitrile, tetrahydrofuran, methyl tert-butyl ether, isopropyl ether, dioxane, acetone, 2-butanone, ethyl acetate, isobutyl acetate, toluene, xylene, chlorobenzene, benzene, N,N-dimethylacetamide, N, N-dimethylformamide, N,N-diethylformamide, N-methylpyrrolidone, dichloromethane, 1,2-dichloroethane, chloroform, n-hexane, n-heptane, cyclohexane, and water, and preferably one member or two or more members selected from methanol, ethanol, tetrahydrofuran, acetonitrile, and n-heptane.

The temperature of the condensation reaction is 0 to 149° C., and preferably 20 to 129° C., and the reaction time is 0.5 to 24 hours, and preferably 1 to 10 hours.

In this method, the acidic substance stated in step (1b) is one member or two or more members of an organic acid, an inorganic acid, a Lewis acid, an acid salt, and other acidic substance. The inorganic acid is sulfuric acid, hydrochloric acid, phosphoric acid, polyphosphoric acid, or phosphotungstic acid. The organic acid is formic acid, acetic acid, propionic acid, oxalic acid, fumaric acid, maleic acid, trifluoroacetic acid, methanesulfonic acid, benzenesulfonic acid, p-toluenesulfonic acid, camphorsulfonic acid, or trifluoromethanesulfonic acid. The Lewis acid is boron trifluoreide ethyl ether, aluminum trichloride, iron trichloride, bismuth trifluoromethanesulfonate, or indium trifluoromethanesulfonate. The acid salt is an acid salt, such as sodium hydrogensulfate, ammonium hydrogensulfate, magnesium hydrogensulfate, pyridinium p-toluenesulfonate, triethylamine hydrochloride, and pyridine hydrochloride. The other acidic substance is silica gel, acidic resin, or acidic resin. Preferably, the acidic substance is p-toluenesulfonic acid, hydrochloric acid, sulfuric acid, sodium hydrogensulfate, or magnesium hydrogensulfate. The molar ratio of the added amount of the compound II to the added amount of the acidic substance is 1:0.2 to 1:10, and preferably 1:0.2 to 1:2.

The hydrolysis reaction is performed in a solvent, and the solvent is one member or two or more members selected from benzene, toluene, chlorobenzene, xylene, acetonitrile, 2-butanone, acetone, 1,2-dimethyl-2-imidazolone, dimethyl sulfoxide, dimethyl sulfone, sulfolane, hexamethylphosphoric triamide, N,N-dimethylformamide, N,N-dimethylacetamide, N,N-diethylformamide, N-methylpyrrolidone, methanol, ethanol, isopropanol, n-butanol, ethylene glycol, polyethylene glycol, dioxane, methyl tert-butyl ether, isopropyl ether, tetrahydrofuran, n-hexane, cyclohexane, dichloromethane, 1,2-dichloroethane, chloroform, and water; and preferably, the solvent is one member or two or more members selected from toluene, acetonitrile, methanol, ethanol, water, tetrahydrofuran, methyl tert-butyl ether, and dichloromethane.

The temperature of the hydrolysis reaction is selected from 20 to 139° C., and the reaction time is 0.5 to 24 hours. Preferably, the reaction temperature is 20 to 100° C., and the reaction time is 0.5 to 10 hours.

The cyclohexenone long-chain alcohol crude product (compound III) refers to such a product on which a purification step has not been performed. When the content of the cyclohexenone long-chain alcohol is 95% or less, the alcohol product is considered to be a crude product. Typically, the content of the cyclohexenone long-chain alcohol crude product (compound III) is 45 to 80% when the method of the present invention is used (HPLC external standard method).

The present invention further provides a method for producing a cyclohexenone long-chain alcohol crude product represented by formula III, which is as shown in the following reaction scheme.

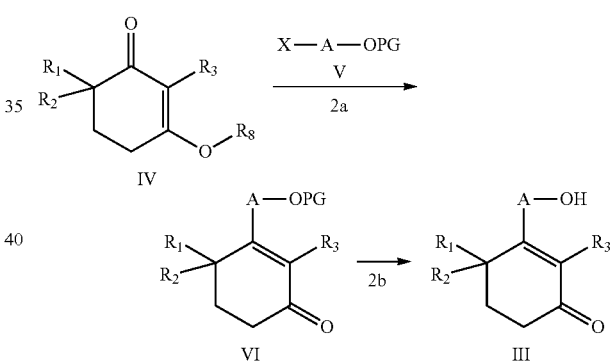

This method comprises the following steps: (2a) subjecting a compound IV and a compound V to a metal-mediated Barbier reaction to generate a compound VI, and (2b) subjecting the compound VI to a deprotection reaction in the presence of an acidic substance to directly remove a protective group thereby obtaining the cyblohexenone long-chain alcohol crude product III, wherein X represents halogen, $R_8$ represents $C_{1-7}$ alkyl, $C_{6-14}$ aryl, or

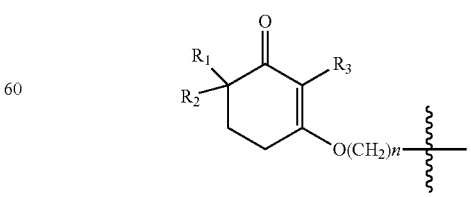

$R_1$, $R_2$, $R_3$, and A are as defined above, n represents 1 to 12, PG represents

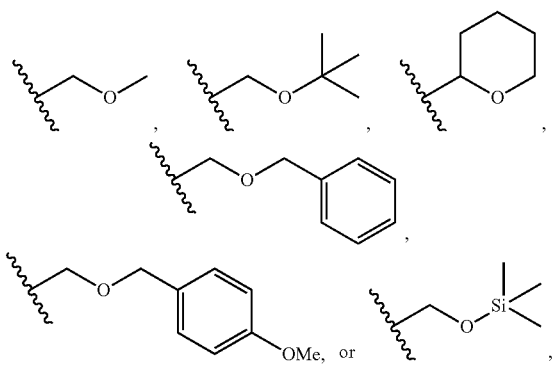

and PG is preferably

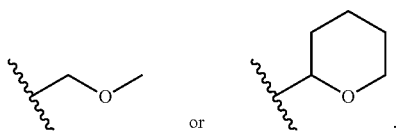

In this method, the metal in step (2a) is lithium, sodium, strontium, magnesium, or zinc, and preferably lithium, strontium, or magnesium; and the molar ratio of the metal to the compound IV is 1:1 to 12:1, and preferably 2:1 to 10:1.

The molar ratio of the compound V to the compound IV is 0.6:1 to 6:1, and preferably 0.8:1 to 4:1.

The Barbier reaction may be performed in the presence or absence of a catalyst, and the catalyst is one member or two or more members selected from tetramethylethylenediamine and hexamethylphosphoric triamide, and the molar ratio of the catalyst to the compound IV is 0.2:1 to 2:1, and preferably 0.4:1 to 1.2:1.

The Barbier reaction is performed in a suitable solvent, and the solvent is one member or two or more members selected from benzene, toluene, chlorobenzene, xylene, tetrahydrofuran, methyltetrahydrofuran, dioxane, methyl tert-butyl ether, n-hexane, n-heptane, cyclohexane, acetonitrile, hexamethylphosphoric triamide, and sulfolane, and preferably one member or two or more members of toluene, xylene, tetrahydrofuran, methyltetrahydrofuran, and n-hexane.

The temperature of the Barbier reaction is selected from −20 to 100° C., preferably −10 to 50° C., and the reaction time is 1 to 36 hours, and preferably 2 to 24 hours.

In this method, the acidic substance in step (2b) is one member or two or more members of methanesulfonic acid, benzenesulfonic acid, p-toluenesulfonic acid, camphorsulfonic acid, pyridinium p-toluenesulfonate, triethylamine hydrochloride, hydrochloric acid, sulfuric acid, phosphoric acid, sodium hydrogensulfate, magnesium hydrogensulfate, an acidic molecular sieve, acidic resin, acetic acid, trifluoroacetic acid, trifluoromethanesulfonic acid, iron trichloride, boron trifluoride ethyl ether, tri silyl chlorosilane, and acetyl chloride, and preferably one member or two or more members of benzenesulfonic acid, p-toluenesulfonic acid, camphorsulfonic acid, pyridinium p-toluenesulfonate, hydrochloric acid, and acetic acid. The molar ratio of the acidic substance to the compound VI is 0.02:1 to 1:1, and preferably 0.05:1 to 0.2:1. The deprotection reaction is performed in a suitable solvent, and the solvent is one member or two or more members of methanol, ethanol, isopropanol, n-butanol, tert-butanol, tert-pentanol, acetonitrile, tetrahydrofuran, methyl tert-butyl ether, isopropyl ether, dioxane, acetone, 2-butanone, ethyl acetate, isobutyl acetate, toluene, xylene, chlorobenzene, benzene, N,N-dimethylacetamide, N,N-dimethylformamide, N,N-diethylformamide, N-methylpyrrolidone, dichloromethane, 1,2-dichloroethane, chloroform, n-hexane, n-heptane, cyclohexane, and water, and preferably one member or two or more members of methanol, ethanol, tetrahydrofuran, acetonitrile, n-heptane, and water.

The temperature of the deprotection reaction is selected from −20 to 100° C., and preferably 0 to 50° C. The reaction time is 0.1 to 10 hours, and preferably 0.5 to 5 hours.

Step (2a) and step (2b) may be separately performed stepwise, or may be performed in a one-pot reaction method.

The present invention further provides a method for producing the cyclohexenone long-chain alcohol crude product represented by formula III. Specifically, a compound IX is subjected to a metal-mediated intermolecular Barbier reaction, thereby obtaining the cyclohexenone long-chain alcohol crude product III. The reaction is as shown in the following reaction scheme:

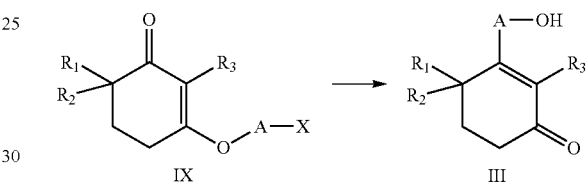

wherein A represents $C_{10-18}$ alkylene, and X represents halogen.

In this method, the metal is lithium, sodium, strontium, magnesium, or zinc, and preferably lithium, strontium, or magnesium.

The molar ratio of the metal to the compound IX is 1:1 to 12:1, and preferably 2:1 to 10:1.

The Barbier reaction may be performed in the presence or absence of a catalyst, and the catalyst is one member or two or more members selected from tetramethylethylenediamine and hexamethylphosphoric triamide. The molar ratio of the catalyst to the compound IX is 0.2 to 2:1, and preferably 0.4 to 1.2:1.

The Barbier reaction is performed in a suitable solvent, and the solvent is one member or two or more members selected from benzene, toluene, chlorobenzene, xylene, tetrahydrofuran, methyltetrahydrofuran, dioxane, methyl tert-butyl ether, n-hexane, n-heptane, cyclohexane, acetonitrile, hexamethylphosphoric triamide, and sulfolane, and preferably one member or two or more members of toluene, xylene, tetrahydrofuran, methyltetrahydrofuran, and n-hexane.

The temperature of the Barber reaction is selected from −20 to 100° C., and preferably −10 to 50° C. The reaction time is 1 to 36 hours, and preferably 2 to 24 hours.

Advantageous Effect

The present invention provides a method for producing and purifying a high-purity cyclohexenone long-chain alcohol, and achieves the production of a cyclohexenone long-chain alcohol by a one-pot method using a metal-mediated Barbier reaction, instead of the Grignard reaction (which requires the separate production of a Grignard reagent alone) disclosed in the literature. The product is purified by a condensation reaction with hydrazine or its derivative, thereby avoiding the operation of column chromatography.

The method of the present invention is performed in a short scheme, is easy to handle and perform, easy to control, provides a high-purity product at a high yield, and is a simple, highly efficient, economical, and industrial production method.

DESCRIPTION OF EMBODIMENTS

The following describes the present invention in more detail with reference to Examples. However, the following embodiments are simply described as examples of the present invention, and these Examples are not intended to limit the present invention in any manner. It is clear that a person skilled in the art can make various replacements or modifications within the scope and concept of the present invention. The present invention should be construed as being intended to cover replacements and modifications made within the scope of the claims attached to this specification.

Preparation of Compound IV

Preparation Example 1: 3-isobutoxy-2,6,6-trimethylcyclohex-2-en-1-one

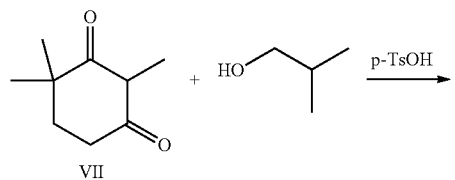

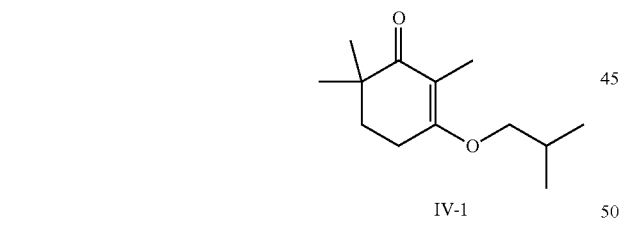

2,4,4-trimethylcyclohexane-1,3-dione VII (80 g, 1 eq) and isobutanol (76.9 g, 2 eq) were added to cyclohexane (400 mL), and p-TSA·H$_2$O (5 g, 0.05 eq) was added thereto, followed by heating under reflux for 16 hours to separate water. The reaction mixture was subjected to a post-treatment and cooled to ambient temperature. The resultant was then sequentially washed with 5% sodium hydroxide (80 mL), water (80 mL), and a saturated sodium chloride solution (80 mL), and dried over anhydrous sodium sulfate, followed by concentration by drying, thereby obtaining 3-isobutoxy-2,6,6-trimethylcyclohex-2-en-1-one (103.65 g, 95%).

$^1$H NMR (400 MHz, CDCl3): δ 3.77 (d, 2H, J=6.4 Hz), 2.55-2.58 (m, 2H), 1.95-2.05 (m, 1H), 1.82 (t, 2H, J=6.4 Hz), 1.72 (s, 3H), 1.11 (s, 6H), 1.01 (d, 6H, J=6.4 Hz).

Preparation Example 2: 3-cyclohexylmethoxy-2,6,6-trimethylcyclohex-2-en-1-one

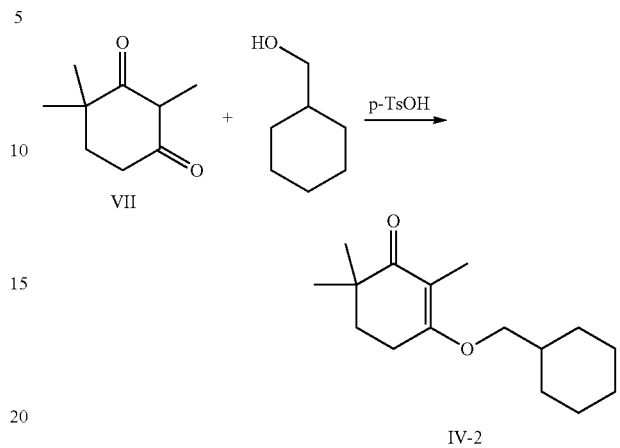

2,4,4-trimethylcyclohexane-1,3-dione VII (10 g, 1 eq) and cyclohexyl methanol (14.8 g, 2 eq) were added to cyclohexane (100 mL), and p-TSA·H$_2$O (0.62 g, 0.05 eq) was added thereto, followed by heating under reflux for 16 hours to separate water. The reaction mixture was subjected to a post-treatment and cooled to ambient temperature. The resultant was then sequentially washed with 5% sodium hydroxide (20 mL), water (20 mL), and a saturated sodium chloride solution (20 mL), and dried over anhydrous sodium sulfate, followed by concentration by drying, and purification by column chromatography, thereby obtaining 3-cyclohexylmethoxy-2,6,6-trimethylcyclohex-2-en-1-one (14.8 q, 91%).

$^1$H NMR (400 MHz, CDCl$_3$) δ 3.80 (d, J=6.9 Hz, 1H), 2.55 (td, 1H, J=6.2, 1.1 Hz), 1.83 (m, 6H), 1.75 (m, 3H), 1.72 (s, 3H), 1.36-1.23 (m, 6H), 1.12 (s, 6H).

Preparation Example 3: 3,3'-(ethyl-1,2-dioxy)-di(2,6,6-trimethylcyclohex-2-en-1-one)

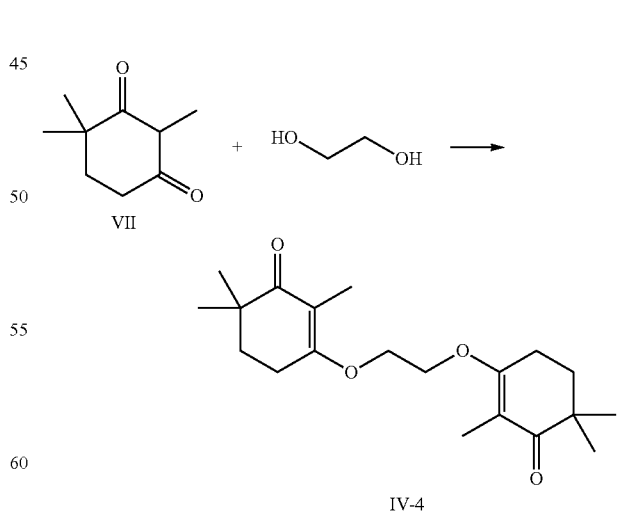

2,4,4-trimethylcyclonexane-1,3-dione VII (5 g, 1 eq), ethylene glycol (1.01 g, 0.5 eq), p-TaAd·H$_2$O (311 mg, 0.05 eq), and toluene (30 mL) were added to a flask, and heated under reflux for 6 hours to separate water. The toluene was dried by rotation, and a saturated sodium hydrogen carbonate solution and dichloromethane were added, followed by extraction. The dichloromethane layer was further washed with a saturated sodium chloride solution once, dried over anhydrous sodium sulfate, and dried by rotation. A mixture solvent of petroleum ether and ethyl acetate was added thereto, and the solids were precipitated, followed by stirring for 3 hours, and further followed by suction filtration and drying, thereby obtaining 3,3'-(ethyl-1,2-dioxy)-di(2,6,6-trimethylcyclohex-2-en-1-one) (4.3 g, 80%). The melting point was 131 to 132° C.

$^1$H NMR (300 MHz, CDCl$_3$) δ 4.25 (s, 4H), 2.57 (t, 4H, J=6.2 Hz), 1.81 (t, 4H, J=6.3 Hz), 1.68 (s, 6H), 1.07 (s, 12H).

Preparation Example 4: 3-methoxy-2,6,6-trimethylcyclohex-2-en-1-one

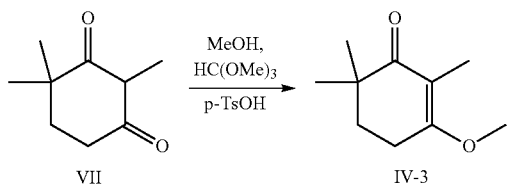

2,4,4-trimethylcyclohexane-1,3-dione VII (2.7 g, 1 eq) and trimethyl orthoformate (2.8 g, 1.5 eq) were added to methanol (40 mL), and p-TSA·H$_2$O (167 mg, 0.05 eq) was added thereto, followed by stirring at room temperature overnight. The reaction mixture was subjected to a post-treatment, and dichloromethane (30 ml) was added for dilution. The resultant was washed sequentially with 5% sodium hydroxide (20 mL), water (10 mL), and a saturated sodium chloride solution (10 mL), and dried over anhydrous sodium sulfate, followed by concentration by drying and purification by column chromatography, thereby obtaining 3-methoxy-2,6,6-trimethylcyclohex-2-en-1-one (2.19 g, 74.4%).

$^1$H NMR (400 MHz, CDCl$_3$); δ 3.81 (s, 3H), 2.55-2.58 (m, 2H), 1.95-2.05 (m, 1H), 1.82 (t, 2H, J=6.4 Hz), 1.72 (s, 3H), 1.11 (s, 6H).

Preparation Example 5: 3,3'-(propyl-1,2-dioxy)-di(2,6,6-trimethylcyclohex-2-en-1-one)

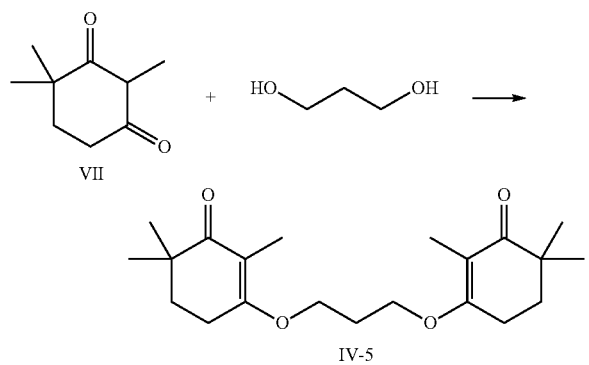

2,4,4-trimethylcyclohexane-1,3-dione VII (5 q, 1 eq), 1,3-propane diol (1.23 g, 0.5 eq), p-TSA·H$_2$O (311 mg, 0.05 eq), and toluene (30 ml) were added to a flask and heated under reflux for 6 hours to separate water. The toluene was dried by rotation, and a saturated sodium hydrogen carbonate aqueous solution and dichloromethane were added, followed by extraction. The dichloromethane layer was further washed with a saturated sodium chloride solution once, dried over anhydrous sodium sulfate, and dried by rotation, followed by column chromatography, thereby obtaining 3,3'-(propyl-1,2-dioxy)-di(2,6,6-trimethylcyclohex-2-en-1-one) (3.96 g, 70%).

$^1$H NMR (400 MHz, CDCl$_3$) δ 4.13 (m, 4H), 2.46 (t, 4H, J=6.2 Hz), 1.81 (t, J=6.2 Hz, 4H), 1.70 (s, 6H), 1.32 (t, 2H, J=6.2 Hz), 1.08 (s, 12H).

Preparation Example 6: 3,3'-(butyl-1,2-dioxy)-di(2,6,6-trimethylcyclohex-2-en-1-one)

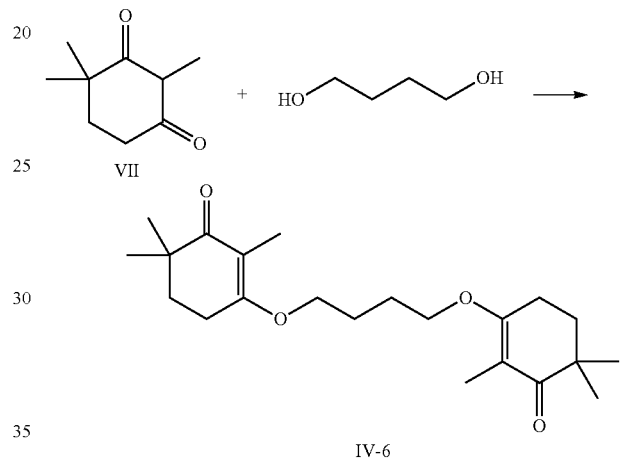

2,4,4-trimethylcyclohexane-1,3-dione VII (5 g, 1 eq) was dissolved in toluene, and p-TSA·H$_2$O (280 mg, 0.05 eq) and 1,4-butanediol (1.46 g, 0.5 eq) were added thereto, followed by heating under reflux to separate water. The reaction mixture was cooled to room temperature, and a saturated sodium carbonate solution was added, followed by the addition of ethyl acetate for extraction. The organic layer was washed with a saturated sodium chloride solution, dried over anhydrous sodium, sulfate, concentrated, and triturated with a petroleum ether ethyl acetate mixture solvent, followed by filtration, thereby obtaining a compound 3,3'-(butyl-1,2-dioxy)-di(2,6,6-trimethylcyclohex-2-en-1-on (4.3 g, 74%). The melting point was 132 to 134° C.

$^1$H NMR (300 MHz, CDCl$_3$) δ 4.10 (m, 4H), 2.57 (t, 4H, J=6.2 Hz), 1.83 (m, 4H), 1.78 (t, 4H, J=6.2 Hz) 1.70 (s, 6H), 1.08 (s, 12H).

Preparation Example 7: 3,3'-(pentyl-1,2-dioxy)-di(2,6,6-trimethyloyclohex-2-en-1-one)

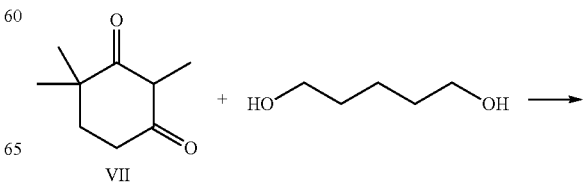

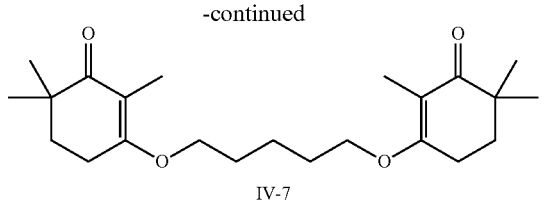

IV-7

2,4,4-trimethylcyclohexane-1,3-dione (5 g, 1 eq) was dissolved in toluene, and p-TSA·H₂O (280 mg, 0.05 eq) and 1,4-pentane diol (1.69 g, 0.5 eq) were added thereto, followed by heating under reflux to separate water. The reaction mixture was cooled to room temperature, and a saturated sodium carbonate solution was added, followed by the addition of ethyl acetate for extraction. The organic layer was washed with a saturated sodium chloride solution, dried over anhydrous sodium, sulfate, and concentrated, followed by column chromatography, thereby obtaining a compound 3,3'-(pentyl-1,2-dioxy)-di(2,6,6-trimethylcyclohex-2-en-1-one) (3.66 g, 60%).

$^1$H NMR (300 MHz, CDCl$_3$) δ 4.10 (m, 4H), 2.57 (t, 4H, J=6.2 Hz), 1.83 (m, 6H), 1.78 (t, 4H, J=6.2 Hz) 1.70 (s, 6H), 1.08 (s, 12H).

Preparation Example 8: 3,3'-(hexyl-1,2-dioxy)-di(2,6,6-trimethylcyclohex-2-en-1-one)

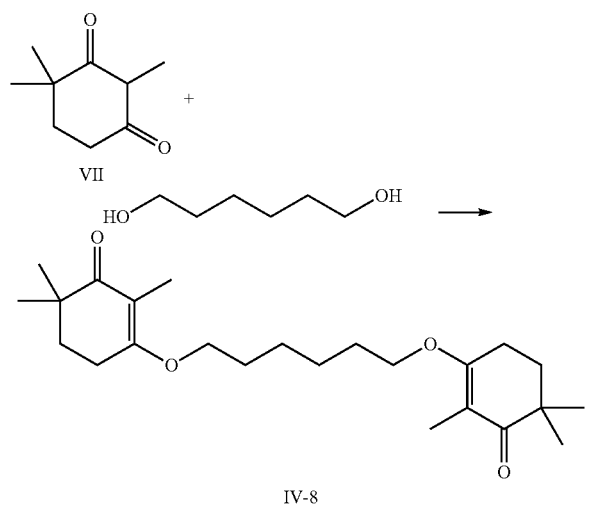

IV-8

2,4,4-trimethylcyclohexane-1,3-dione VII (5 g, 1 eq) and 1,6-hexane diol (1.92 g, 0.5 eq) were dissolved in toluene (50 mL), and camphorsulfonic acid (1.5 g, 0.2 eq) was added thereto, followed by heating under reflux overnight to separate water. The reaction mixture was cooled to ambient temperature, and washed individually with 5% sodium hydroxide (20 mL), water (10 mL), and a saturated sodium chloride solution (20 mL). The resultant was dried over anhydrous sodium sulfate, filtered, and dried by concentration, followed by trituration with methanol, thereby obtaining 3,3'-(hexyl-1,2-dioxy)-di(2,6,6-trimethylcyclohex-2-en-1-one) (4.7 g, 89%) as white solids. The melting point was 92 to 94° C.

$^1$H NMR (300 MHz, CDCl$_3$) δ 4.10 (m, 4H), 2.47 (t, 4H, J=6.2 Hz), 1.88 (m, 4H), 1.78 (t, 4H, J=6.2 Hz) 1.70 (s, 6H), 1.32 (m, 4H) 1.08 (s, 12H).

Preparation of Compound IX

Preparation Example 9: 3-(15-chloropentadecyloxy-2,6,6-trimethylcyclohex-2-en-1-one)

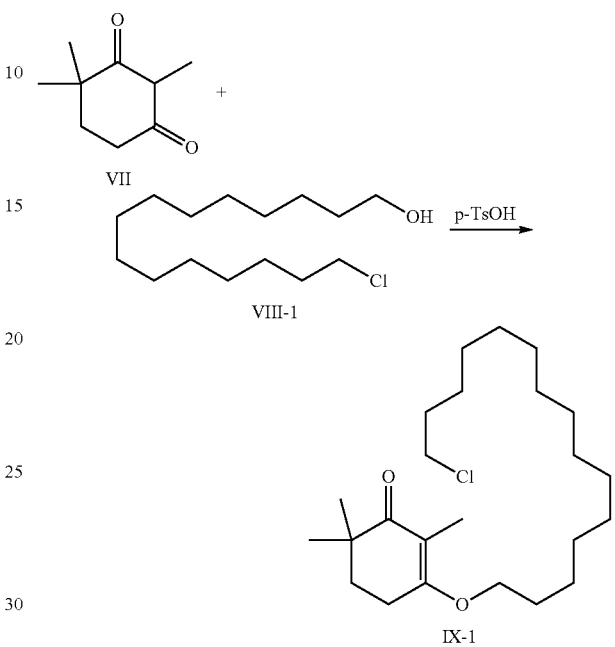

IX-1

2,4,4-trimethylcyclohexane-1,3-dione VII (1.3 g, 1.1 eq) and 15-chloropentadecanol VIII-1 (2 g, 1 eq) were added to cyclohexane (50 mL), and p-TSA·H₂O (70 mg, 0.05 eq) was added thereto, followed by heating under reflux for 16 hours to separate water. The reaction mixture was subjected to a post-treatment, cooled to ambient temperature, and sequentially washed with 5% sodium hydroxide (20 mL), water (10 mL), and a saturated sodium chloride solution (10 mL). The resultant was dried over anhydrous sodium sulfate and dried by concentration, thereby obtaining 3-(15-chloropentadecyloxy)-2,6,6-trimethylcyclohex-2-en-1-one (2.46 g, 80.9%).

$^1$H NMR (400 MHz, CDCl$_3$): δ 3.97 (t, 2H, J=6.8 Hz), 3.45 (m, 2H, J=6.8 Hz), 2.54-2.55 (m, 2H), 1.78-1.84 (m, 4H), 1.68 (s, 3H), 1.39-1.41 (m, 4H), 1.22-1.35 (m, 21H), 1.08 (s, 6H).

Preparation Example 10: 3-(15-bromopentadecyloxy)-2,6,6-trimethylcyclohex-2-en-1-one

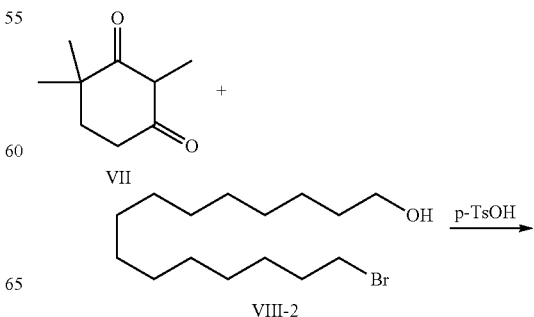

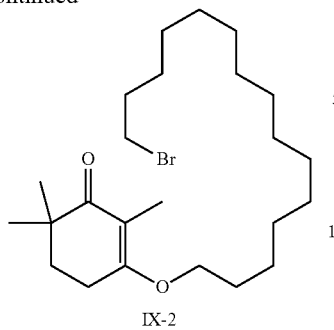

IX-2

2,4,4-trimethylcyclohexane-1,3-dione VII (1.5 g, 1 eq) and 15-bromopentadecanol VIII-2 (2.5 g, 1 eq) were added to cyclohexane (50 mL), and p-TSA·H$_2$O (80 mg, 0.05 eq) was added thereto, followed by heating under reflux for 16 hours to separate water. The reaction mixture was subjected to a post-treatment, cooled to ambient temperature, and sequentially washed with 5% sodium hydroxide (20 mL), water (10 mL), and a saturated sodium chloride solution (10 mL). The resultant was dried over anhydrous sodium sulfate and dried by concentration, thereby obtaining 3-(15-bromopentadecyloxy)-2,6,6-trimethylcyclohex-2-en-1-one (3.37 g, 93.6%).

$^1$H NMR (400 MHz, CDCl$_3$): δ 3.97 (t, 2H, J=6.8 Hz), 3.40 (m, 2H, J=6.8 Hz), 2.54-2.55 (m, 2H), 1.78-1.84 (m, 4H), 1.68 (s, 3H), 1.39-1.41 (m, 4H), 1.22-1.35 (m, 21H), 1.08 (s, 6H).

Preparation Example 11: 3-(15-odopentadecyloxy)-2,6,6-trimethylcyclohex-2-en-1-one

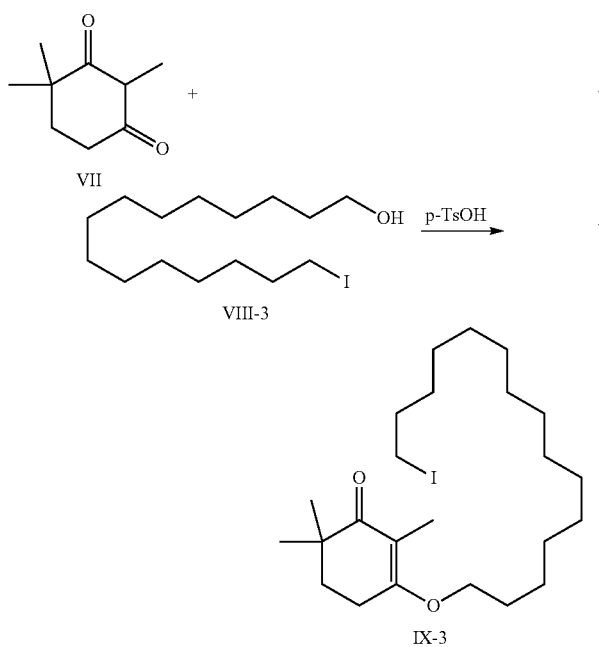

IX-3

2,4,4-trimethylcyclohexane-1,3-dione VII (2.55 g, 1.2 eq) and 15-iodopentadecanol VIII-3 (5 g, 1 eq) were added to cyclohexane (50 mL), and p-TSA·H$_2$O (130 mg, 0.05 eq) was added thereto, followed by heating under reflux for 16 hours to separate water. The reaction mixture was subjected to a post-treatment, cooled to ambient temperature, sequentially washed with 5% sodium hydroxide (20 mL), water (10 mL), and a saturated sodium chloride solution (10 mL). The resultant was dried over anhydrous sodium sulfate and dried by concentration, thereby obtaining 3-(15-iodopentadecyloxy)-2,6,6-trimethylcyclohex-2-en-1-one (5.3 g, 76.6%).

$^1$H NMR (400 MHz, CDCl$_3$): δ 3.97 (t, 2H, J=8.4 Hz), 3.18 (in, 2H, J=9.6 Hz), 2.54 (t, 2H, J=8.4 Hz), 1.78-1.83 (m, 2H), 1.68 (s, 3H), 1.21-1.50 (m, 25H), 1.08 (s, 6H).

Preparation of Compound VI

Example 1

2,4,4-trimethyl-3-[15-(tetrahydro-2-hydro-pyranyl)-2-oxy-pentadecyl]cyclohex-2-en-1-one

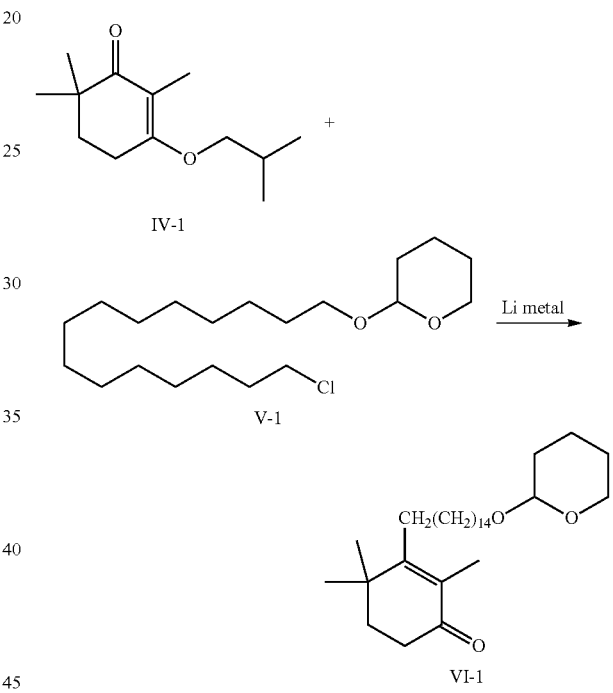

3-isobutoxy-2,6,6-trimethylcyclonex-2-en-1-one IV-1 (3 g, 1 eq) and 2-(15-chloropentadecyl)oxytetrahydro-2-hydropyran V-1 (5.44 g, 1.1 eq) were added to a three-necked flask, and replacement by nitrogen gas was performed three times. Tetrahydrofuran or toluene was added thereto, and replacement by nitrogen as was performed three times. Li (297 g, 3 eq) was added thereto, and replacement by nitrogen gas was performed three times. The temperature was controlled to 25 to 30° C., and the reaction was allowed to proceed for 16 hours. TLC confirmed that the starting materials almost, completely reacted. The reaction mixture was cooled to 10 to 20° C., and saturated ammonium chloride (30 mL) was added dropwise, followed by the addition of water (30 mL). The mixture was stirred for 5 minutes and separated into layers. The organic layer was washed with 0.5M hydrochloric acid (20 mL), and allowed to stand to separate into layers. The resultant was washed with a saturated sodium chloride solution and dried over anhydrous sodium sulfate, followed by concentration by drying, thereby obtaining 2,4,4-trimethyl-3-[15-(tetrahydro- 2-hydro-pyranyl)-2-oxy-pentadecyl]cyclohex-2-en-1-one (crude product: 6.6 g, 103%) as a lime green oil.

¹H NMR (400 MHz, CDCl₃) δ 4.59 (dd, 1H, J=4.5, 2.7 Hz), 3.89 (ddd, 1H, J=11.1, 7.4, 3.4 Hz), 3.75 (dt, 1H, J=9.5, 6.9 Hz), 3.59-3.47 (m, 1H), 3.40 (dt, 1H, J=9.6, 6.7 Hz), 2.51-2.43 (m, 2H), 2.23-2.14 (m, 2H), 1.89-1.80 (m, 4H), 1.77 (s, 3H), 1.67-1.48 (m, 6H), 1.49-1.28 (m 23H), 1.17 (s, 6H), 1.14 (d, 1H, J=14.2 Hz).

Example 2

2,4,4-trimethyl-3-[15-(tetrahydro-2-hydro-pyranyl)-2-oxy-pentadecyl]cyclohex-2-en-1-one

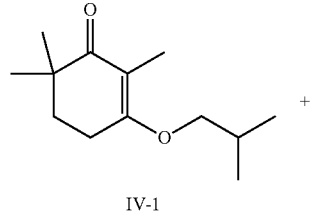

IV-1

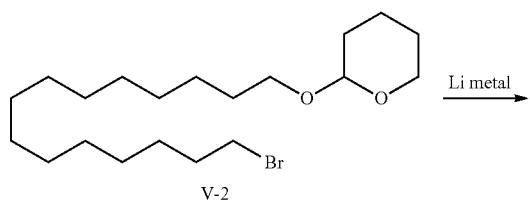

V-2

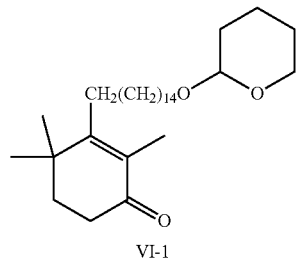

VI-1

3-isobutoxy-2,6,6-trimethylcyclohex-2-en-1-one (5 g, 1 eq) and 2-(15-bromopentadecyl)oxytetrahydro-2-hydro-pyran (12.1 g, 1.3 eq) were dissolved in THF and toluene, and replacement, by nitrogen gas was performed. Li (500 mg, 3 eq) was added thereto, and the mixture was stirred at 15 to 25° C. overnight. The next day, TLC confirmed that the starting materials completely reacted. The reaction mixture was cooled to about 20° C., and a saturated ammonium chloride solution (20 mL) was added dropwise to the reaction mixture, followed by supplementation with water (20 mL) and stirring to separate the mixture into layers. The organic layer was washed with 0.5N hydrochloric acid (20 mL), and washed with water, followed by drying and concentration by drying, thereby obtaining 2,4,4-trimethyl-3-[15-(tetrahydro-2-hydro-pyranyl)-2-oxy-pentadecyl]cyclohex-2-en-1-one (crude product: 13.5 g, 126%) as an oil.

Example 3

2,4,4-trimethyl-3-[15-(tetrahydro-2-hydro-pyranyl)-2-oxy-pentadecyl]cyclohex-2-en-1-one

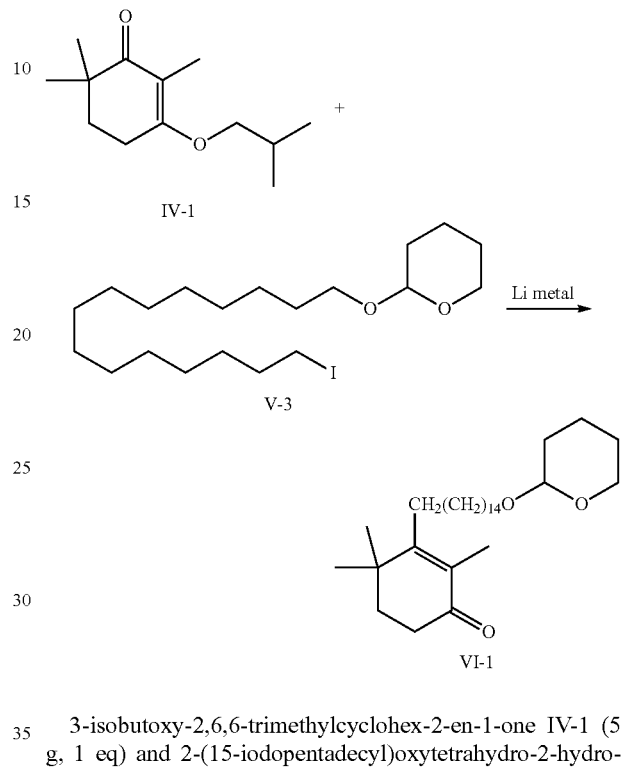

3-isobutoxy-2,6,6-trimethylcyclohex-2-en-1-one IV-1 (5 g, 1 eq) and 2-(15-iodopentadecyl)oxytetrahydro-2-hydro-pyran V-3 (13.6 g, 1.3 eq) were dissolved in THF and toluene, and replacement by nitrogen gas was performed. Li (500 mg, 3 eq) was added thereto, and the mixture was stirred at 15 to 25° C. overnight. The next day, TLC confirmed that the starting materials completely reacted. The reaction mixture was cooled to about 20° C., and a saturated ammonium chloride solution (20 ml) was added dropwise to the reaction mixture, followed by supplementation with water (20 mL) and stirring to separate the mixture into layers. The organic layer was washed with 0.5N hydrochloric acid (20 mL) and washed with water, followed by drying, and concentration by drying, thereby obtaining 2,4,4-trimethyl-3-[15-(tetrahydro-2-hydro-pyranyl)-2-oxy-pentadecyl]cyclohex-2-en-1-one (13.5 g, 126%) as an oil.

Example 4

3-(15-methoxymethyleneoxy-pentadecyl)-2,4,4-trimethylcyclohex-2-en-1-one

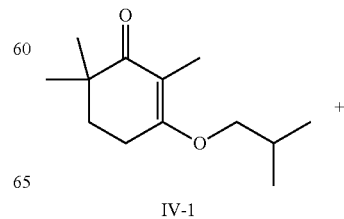

IV-1

-continued

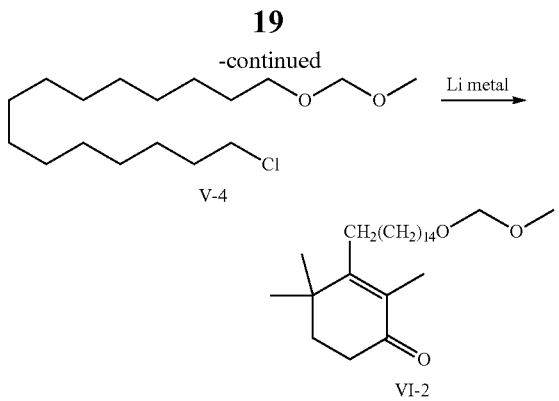

3-isobutoxy-2,6,6-trimethylcyclohex-2-en-1-one IV-1 (3 g, 1 eq) and 1-chloro-15-methoxymethyleneoxypentadecane V-4 (4.82 g, 1.1 eq) were added to a three-necked flask, and replacement by nitrogen gas was performed three times. Tetrahydrofuran and toluene were added thereto, and replacement by nitrogen gas was performed three times. Li (297 g, 3 eq) was added thereto, and replacement by nitrogen gas was performed three times. The temperature was controlled to 25 to 30° C., and a reaction was allowed to proceed for 16 hours. TLC confirmed that the starting materials almost completely reacted. The reaction mixture was cooled to 10 to 20° C. and a saturated ammonium chloride solution (30 mL) was added dropwise thereto, followed by the addition of water (30 mL) and stirring for 5 minutes to separate the mixture into layers. The organic layer was washed with 0.5M hydrochloric acid (20 mL) and allowed to stand to separate into layers. The resultant was washed with a saturated sodium chloride solution, dried over anhydrous sodium sulfate, and dried by concentration, thereby obtaining 3-(15-methoxymethyleneoxy-pentadecyl)-2,4,4-trimethylcyclohex-2-en-1-one (crude product: 6.8 g, 117%) as a lime green oil.

$^1$H NMR (400 MHz, CDCl$_3$) δ 4.55 (s, 2H), 3.49 (t, 2H, J=7.4 Hz), 3.16 (s, 3H), 2.92 (t, 2H, J 5.9 Hz), 2.30-2.22 (m, 2H), 1.99 (s, 2H), 1.63-1.68 (m, 2H), 1.52-1.42 (m, 2H), 1.42-1.31 (m, 3H), 1.34-1.25 (m, 22H), 1.21 (s, 6H).

Example 5

2,4,4-trimethyl-3-[15-(tetrahydro-2-hydro-pyranyl)-2-oxy-pentadecyl]cyclohex-2-en-1-one

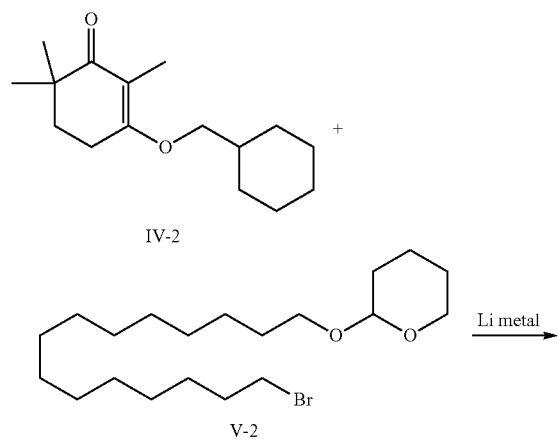

-continued

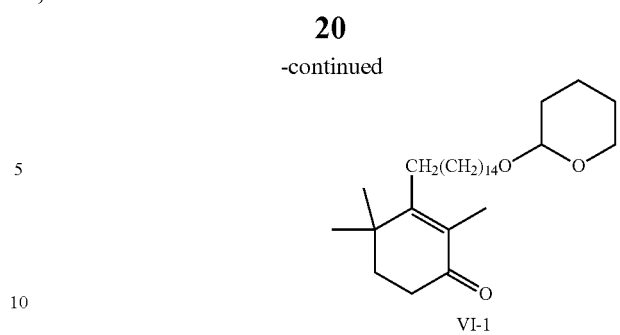

3-cyclohexylmethoxy-2,6,6-trimethylcyclonex-2-en-1-one IV-2 (2 g, 1 eq) and 2-(15-bromopentadecyl)oxytetrahydro-2-hydro-pyran V-2 (3.44 g, 1.1 eq) were dissolved in THF (30 mL), and replacement by nitrogen gas was performed. Li (166 mg, 3 eq) was added thereto, and the mixture was stirred at 20 to 30° C. overnight. The next day, TLC confirmed that the starting materials completely reacted. A saturated ammonium chloride solution (10 mL) and water (10 mL) were added dropwise to the reaction mixture, and the mixture was stirred for 10 minutes, followed by separation into layers. EA was added to the organic layer for dilution, and the resultant was washed with water, washed with a saturated sodium chloride solution, and dried, followed by concentration by drying, thereby obtaining 2,4,4-trimethyl-3-[15-(tetrahydro-2-hydro-pyranyl)-2-oxypentadecyl]cyclohex-2-en-1-one (crude product: 4.6 g, 128%) as an oil.

Example 6

2,4,4-trimethyl-3-[15-(tetrahydro-2-hydro-pyranyl)-2-oxy-pentadecyl]cyclohex-2-en-1-one

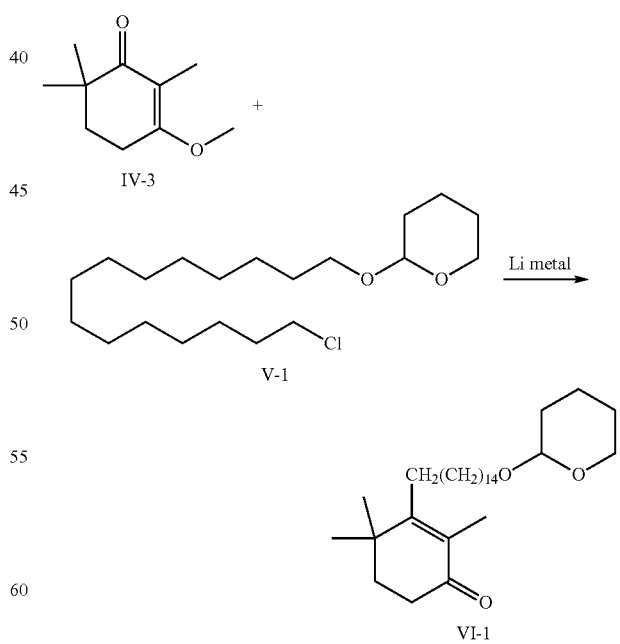

3-isomethoxy-2,6,6-trimethylcyclohex-2-en-1-one IV-3 (10 g, 1 eq) and 2-(15-chloropentadecyl)oxytetrahydro-2-hydro-pyran V-1 (22.7 g, 1.1 eq) were added to a three-necked flask, and replacement by nitrogen gas was performed three times. Tetrahydrofuran or toluene was added thereto, and replacement by nitrogen gas was performed three times. Li (1.24 g, 3 eq) was added thereto, and replacement by nitrogen gas was performed three times. The temperature was controlled to 25 to 30° C., and a reaction was allowed to proceed for 16 hours. TLC confirmed that the starting materials almost completely reacted. The reaction mixture was cooled to 10 to 20° C., and a saturated ammonium chloride solution (100 mL) was added dropwise thereto, followed by the addition of water (100 mL) and stirring for 5 minutes to separate the mixture into layers. The organic layer was washed with 0.5M hydrochloric acid (60 mL), and allowed to stand to separate into layers. The resultant was washed with a saturated sodium chloride solution, dried over anhydrous sodium sulfate, and dried by concentration, thereby obtaining 2,4,4-trimethyl-3-[15-(tetrahydro-2-hydro-pyranyl)-2-oxy-pentadecyl]cyclohex-2-en-1-one (crude product: 28.2 g, 106) as a lime green oil.

Preparation of Compound III

Example 7

3-(15-hydroxypentadecyl)-2,4,4-trimethylcyclohex-2-en-1-one

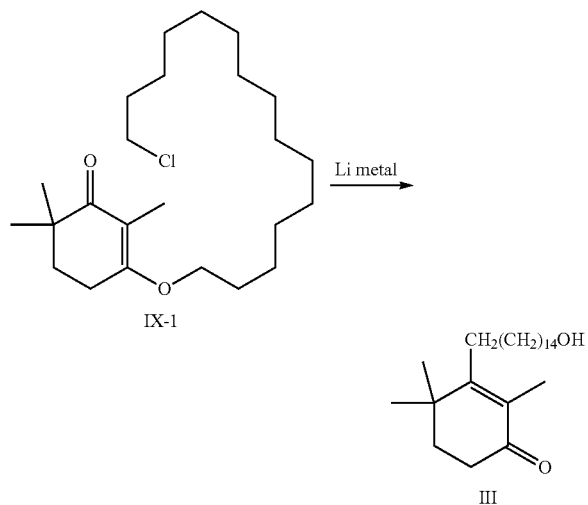

3-(15-chloropentadecyloxy-2,6,6-trimethylcyclohex-2-en-1-one) IX-1 (2 g) was added to anhydrous tetrahydrofuran (20 mL), and protected by nitrogen gas. Lithium (104 mg, 3 eq) was added thereto, and replacement by nitrogen gas was performed, followed by stirring at room temperature for more than 16 hours. TLC confirmed that the starting materials completely reacted. A saturated ammonium chloride solution (10 mL) and water (10 mL) were added dropwise to the reaction mixture, and the mixture was stirred for 10 minutes to separate the mixture into layers. EA was added to the organic layer for dilution, and the resultant was washed with water, washed with a saturated sodium chloride solution, and dried, thereby obtaining a 3-(15-hydroxypentadecyl)-2,4,4-trimethylcyclohex-2-en-1-one crude product as an oil (1.82 g, 100%). The content (HPLC external standard method) was 61.2%.

Example 8

3-(15-hydroxypentadecyl)-2,4,4-trimethylcyclohex-2-en-1-one

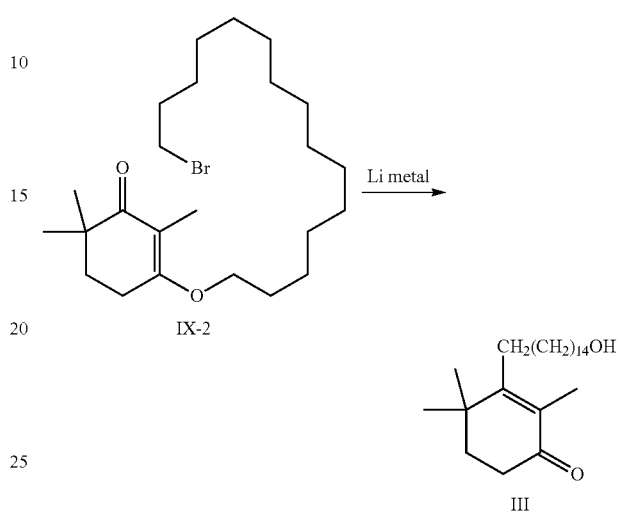

3-(15-bromopentadecyloxy)-2,6,6-trimethylcyclohex-2-en-1-one IX-2 (2 g) was added to anhydrous tetrahydrofuran (20 mL), and protected by nitrogen gas. Lithium (94 mg, 3 eq) was added thereto, and replacement by nitrogen gas was performed, followed by stirring at room temperature for more than 16 hours. TLC confirmed that the starting materials completely reacted. A saturated ammonium chloride solution (10 mL) and water (10 mL) were added dropwise to the reaction mixture, and the mixture was stirred for 10 minutes to separate the mixture into layers. EA was added to the organic layer for dilution, and the resultant was washed with water, washed with a saturated sodium chloride solution, and dried, thereby obtaining a 3-(15-hydroxypentadecyl)-2,4,4-trimethylcyclohex-2-en-1-one crude product as an oil (1.67 g, 102%). The content (HPLC external standard method) was 63.3%.

Example 9

3-(15-hydroxypentadecyl)-2,4,4-trimethylcyclohex-2-en-1-one

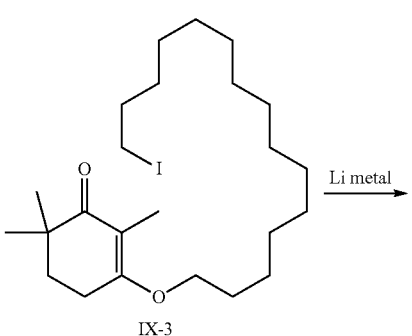

-continued

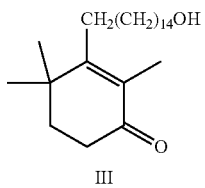

III 3-(15-iodopentadecyloxy)-2,6,6-trimethylcyclohex-2-en-1-one IX-3 (2 g) was added to anhydrous tetrahydrofuran (20 and protected by nitrogen gas. Lithium (85 mg, 3 eq) was added thereto, and replacement by nitrogen gas was performed, followed by stirring at room temperature for more than 16 hours. TLC confirmed that the starting materials completely reacted. A saturated ammonium chloride (10 mL) and water (10 mL) were added dropwise to the reaction mixture, and the mixture was stirred for 10 minutes to separate the mixture into layers. EA was added to the organic layer for dilution, and the resultant was washed with water, washed with a saturated sodium chloride solution, and dried, thereby obtaining a 3-(15-hydroxypentadecyl)-2,4,4-trimethylcyclohex-2-en-1-one crude product as an oil (1.50 g, 101%). The content (HPLC external standard method) was 60.5%.

Preparation of Compound VI

Example 10

2,4,4-trimethyl-3-[15-(tetrahydro-2-hydro-pyranyl)-2-oxy-pentadecyl]cyclohex-2-en-1-one

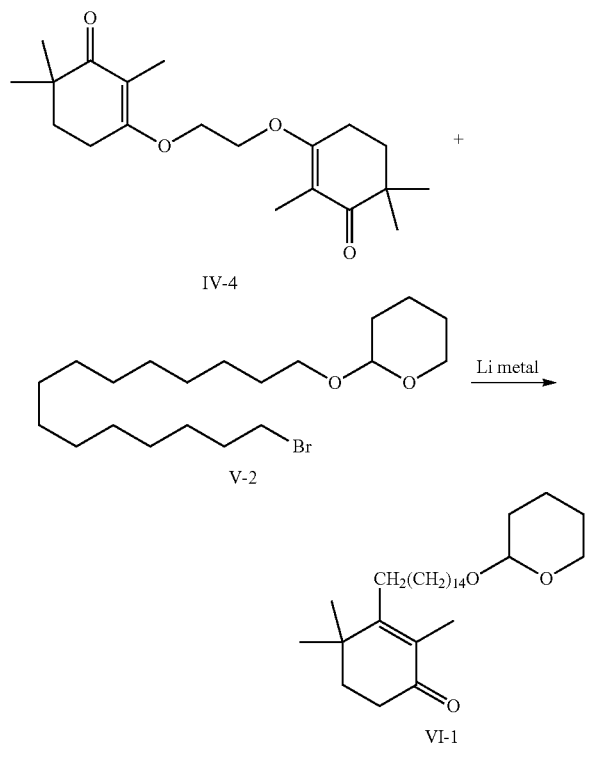

3,3'-(ethyl-1,2-dioxy)-di(2,6,6-trimethylcyclohex-2-en-1-one) IV-3 (5 g, 1 eq) and 2-(15-bromopentadecyl)oxytetrahydro-2-hydro-pyran (12.8 g, 2.2 eq) were dissolved in THF (50 mL), and replacement by nitrogen gas was performed. Li (623 mg, 6 eq) was added thereto, and stirred at 25 to 35° C. overnight. The next day, TLC confirmed the end of the reaction. The reaction mixture was cooled to 0 to 10° C., and a saturated ammonium chloride (20 mL) and water (10 mL) were added dropwise, followed by separation into layers. The organic layer was washed with 0.5N hydrochloric acid (20 mL), washed with a saturated sodium chloride solution, and dried over anhydrous sodium sulfate, followed by filtration and concentration by drying, thereby obtaining a 2,4,4-trimethyl-3-[15-(tetrahydro-2-hydro-pyranyl)-2-oxy-pentadecyl]cyclohex-2-en-1-one crude product (13.9 g, 104%).

Example 11

2,4,4-trimethyl-3-[15-(tetrahydro-2-hydro-pyranyl)-2-oxy-pentadecyl]cyclohex-2-en-1-one

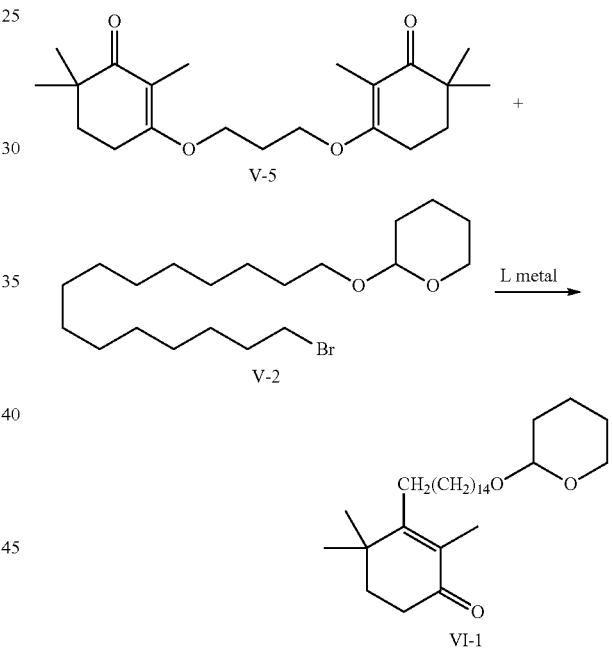

3,3'-(propyl-1,2-dioxy)-di(2,6,6-trimethylcyclohex-2-en-1-one) (5 g, 1 eq) and 2-(15-bromopentadecyl)oxytetrahydro-2-hydro-pyran (12.4 g, 2.2 eq) were dissolved in THF (50 mL), and replacement by nitrogen gas was performed. Li (597 mg, 6 eq) was added thereto, and the mixture was stirred at 25 to 35° C. overnight. The next day, TLC confirmed the end of the reaction. The reaction mixture was cooled to 0 to 10° C., and a saturated ammonium chloride (20 mL) and water (10 mL) were added dropwise to separate the mixture into layers. The organic layer was washed with 0.5N hydrochloric acid (20 mL), washed with a saturated sodium chloride solution, dried over anhydrous sodium sulfate, and filtered, followed by concentration by drying, thereby obtaining 2,4,4-trimethyl-3-[15-(tetrahydro-2-hydro-pyranyl)-2-oxy-pentadecyl]cyclohex-2-en-1-one (crude product: 7.05 g, 109%).

Example 12

2,4,4-trimethyl-3-[15-(tetrahydro-2-hydro-pyranyl)-2-oxy-pentadecyl]cyclohex-2-en-1-one

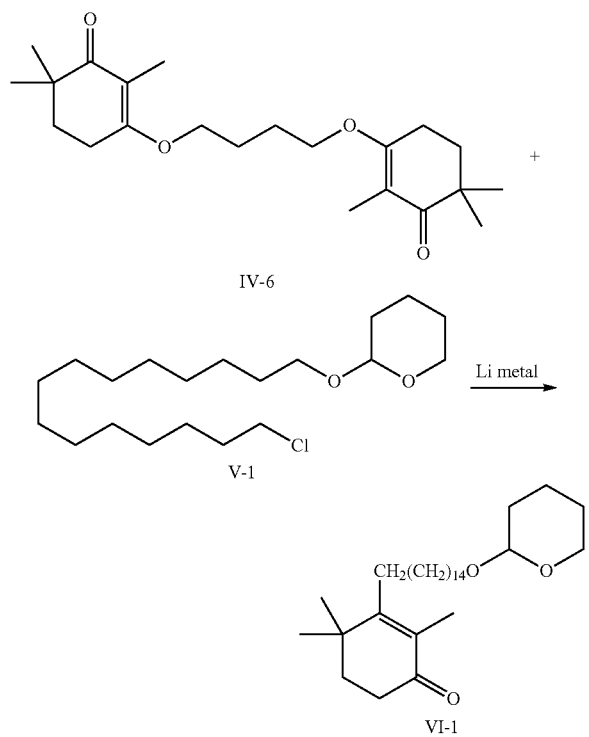

3,3'-(butyl-1,2-dioxy)-di(2,6,6-trimethylcyclohex-2-en-1-one) IV-6 (5 g, 1 eq) and 2-(15-chloropentadecyl)oxytetrahydro-2-hydro-pyran V-1 (10.5 g, 2.2 eq) were dissolved in TEF (50 mL), and replacement by nitrogen gas was performed. Li (574 mg, 6 eq) was added thereto, and the mixture was stirred at 25 to 35° C. overnight. The next day, TLC confirmed the end of the reaction, and the reaction mixture was cooled to 0 to 10° C. A saturated ammonium chloride (20 mL) and water (10 mL) were added dropwise thereto to separate the mixture into layers. The organic layer was washed with 0.5N hydrochloric acid (20 mL), washed with a saturated sodium chloride solution, dried over anhydrous sodium sulfate, and filtered, followed by concentration by drying, thereby obtaining 2,4,4-trimethyl-3-[15-(tetrahydro-2-hydro-pyranyl)-2-oxy-pentadecyl]cyclohex-2-en-1-one (crude product: 7.1 g, 115%).

Example 13

2,4,4-trimethyl-3-[15-(tetrahydro-2-hydro-pyranyl)-2-oxy-pentadecyl]cyclohex-2-en-1-one

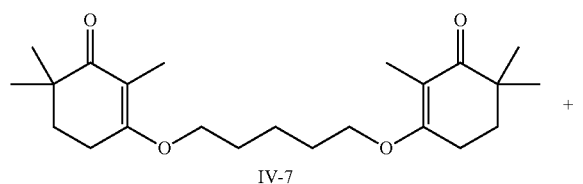

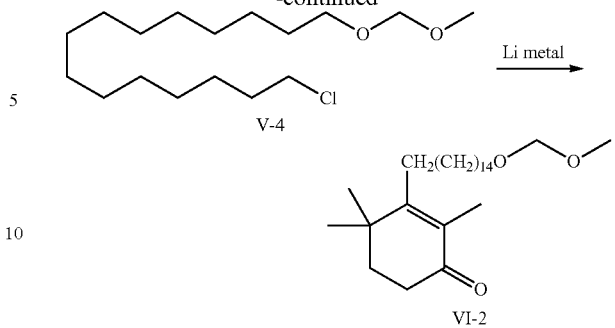

3,3'-(pentyl-1,1-dioxy)-di(2,6,6-trimethylcyclohex-2-en-1-one) IV-7 (5 g, 1 eq) and 1-chloro-15-methoxymethyleneoxypentadecane V-4 (8.97 g, 2.2 eq) were dissolved in THF (50 mL), and replacement by nitrogen gas was performed. Li (553 mg, 6 eq) was added thereto, and the mixture was stirred at 25 to 35° C. overnight. The next day, TLC confirmed the end of the reaction, and the reaction mixture was cooled to 0 to 10° C. Saturated ammonium chloride (20 mL) and water (10 mL) were added dropwise to separate the mixture into layers. The organic layer was washed with 0.5N hydrochloric acid (20 mL), washed with a saturated sodium chloride solution, dried over anhydrous sodium sulfate, and filtered, followed by concentration by drying, thereby obtaining 3-(15-methoxymethyleneoxy-pentadecyl)-2,4,4-trimethylcyclohex-2-en-1-one (crude product: 5.5 g, 101%).

Example 14

2,4,4-trimethyl-3-[15-(tetrahydro-2-hydro-pyranyl)-2-oxy-pentadecyl]cyclohex-2-en-1-one

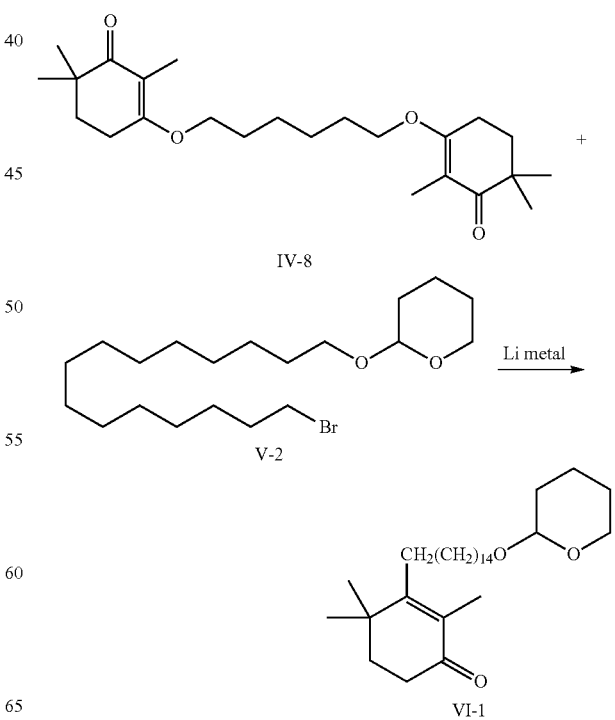

3,3'-(hexyl-1,2-dioxy)-di(2,6,6-trimethylcyclonex-2-en-1-one) IV-8 (5 g, 1 eq) and 2-(15-bromopentadecyl)oxytetrahydro-2-hydro-pyran (12.1 g, 2.2 eq) were dissolved in THF (50 mL), and replacement by nitrogen gas was performed. Li (530 mg, 6 eq) was added thereto, and the mixture was stirred at 25 to 35° C. overnight. The next day, TLC confirmed the end of the reaction, and the reaction mixture was cooled to 0 to 10° C. Saturated ammonium chloride (20 mL) and water (10 mL) were added dropwise to separate the mixture into layers. The organic layer was washed with 0.5N hydrochloric acid (20 mL), washed with a saturated sodium chloride solution, dried over anhydrous sodium sulfate, and filtered, followed by concentration by drying, thereby obtaining a 2,4,4-trimethyl-3-[15-(tetrahydro-2-hydro-pyranyl)-2-oxy-pentadecyl]cyclohex-2-en-1-one crude product (13.6 g, 118%).

Preparation of Compound III

Example 15

3-(15-hydroxypentadecyl)-2,4,4-trimethylcyclohex-2-en-1-one

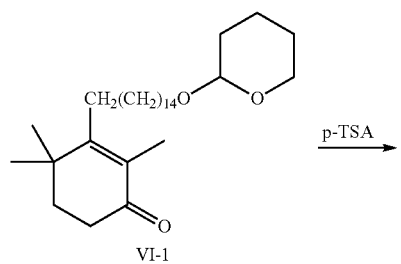

2,4,4-trimethyl-3-[15-(tetrahydro-2-hydro-pyranyl)-2-oxy-pentadecyl]cyclohex-2-en-1-one VI-1 (51.7 g, 1 eq) was dissolved in methanol (200 mL), and p-TSA·H$_2$O (1.8 g, 0.1 eq) was added thereto, followed by stirring for 3 hours. Sodium hydrogen carbonate (2 g) was added, and the mixture was stirred for 10 minutes, and dried by concentration. Dichloromethane (100 mL) and water (50 mL) were added thereto to separate the mixture into phases. The organic layer was washed with a saturated sodium chloride solution (50 mL), dried over anhydrous sodium sulfate, and dried by concentration, thereby obtaining 3-(15-hydroxypentadecyl)-2,4,4-trimethylcyclohex-2-en-1-one (crude product: 39.8 g). The content (HPLC external standard method) was 70.2%.

Example 16

3-(15-hydroxypentadecyl)-2,4,4-trimethylcyclohex-2-en-1-one

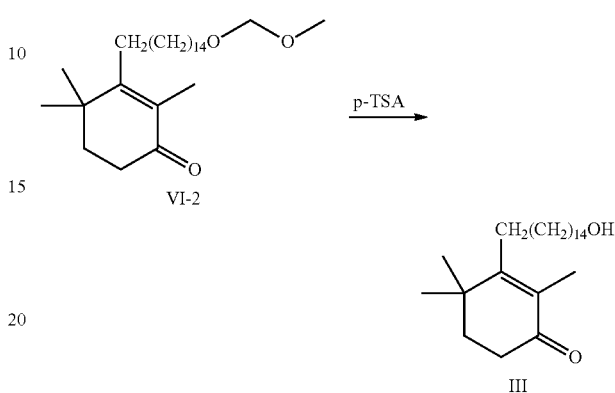

3-(15-methoxymethyleneoxy-pentadecyl)-2,4,4-trimethylcyclohex-2-en-1-one VI-2 (50 g, 1 eq) was dissolved in methanol (200 mL), and p-TSA·H$_2$O (2.11 g, 0.1 eq) was added thereto, followed by stirring for 3 hours. Sodium hydrogen carbonate (2 g) was added, and the mixture was stirred for 10 minutes, and dried by concentration. Dichloromethane (100 mL) and water (50 mL) were added to separate the mixture into layers. The organic layer was washed with a saturated sodium chloride solution (50 mL), dried over anhydrous sodium sulfate, and dried by concentration, thereby obtaining 3-(15-hydroxypentadecyl)-2,4,4-trimethylcyclohex-2-en-1-one (crude product: 42.8 g). The content (HPLC external standard method) was 69.6%.

Example 17

3-(15-hydroxypentadecyl)-2,4,4-trimethylcyclohex-2-en-1-one (one-pot method)

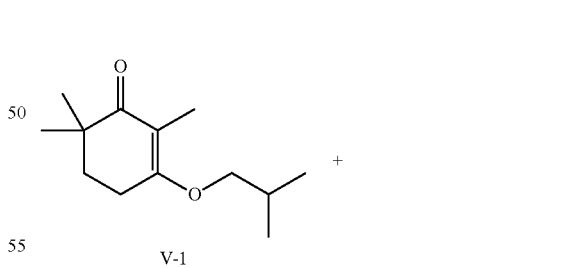

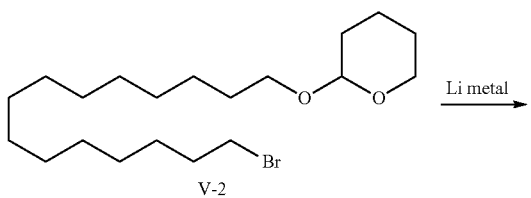

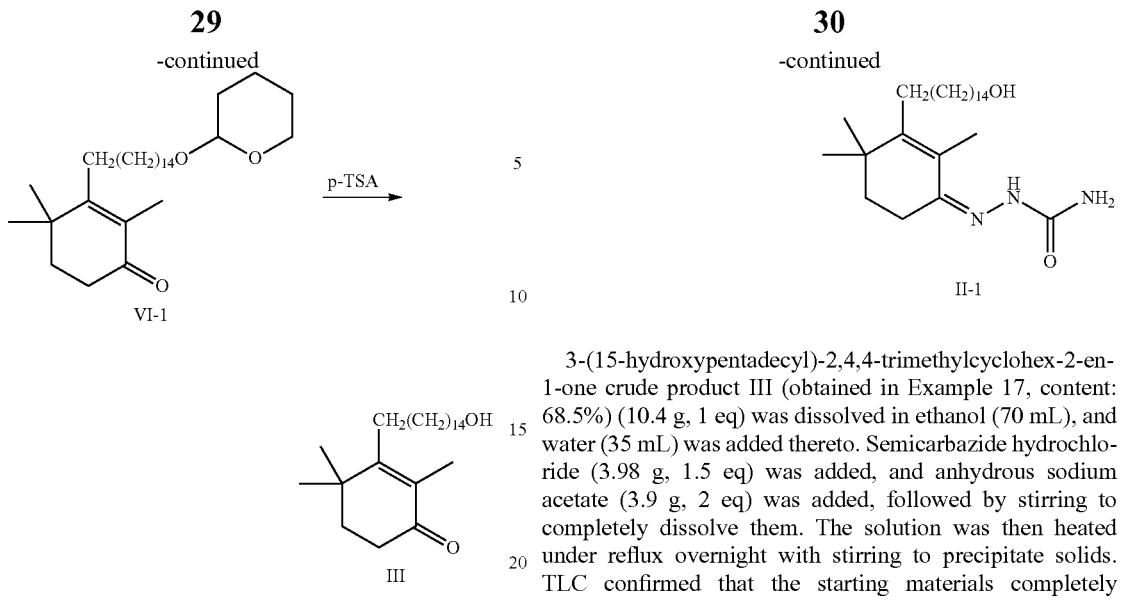

3-isobutoxy-2,6,6-trimethylcyclohex-2-en-1-one (50 g, 1 eq) and 2-(15-bromopentadecyl)oxytetrahydro-2-hydropyran V-2 (121 g, 1.3 eq) were dissolved in THF, and replacement by nitrogen gas was performed. Li (5 g, 3 eq) was added thereto, and the mixture was stirred at 15 to 25° C. overnight. The next day, TLC confirmed that the starting materials completely reacted. The reaction mixture was cooled to about 20° C., and a saturated ammonium chloride solution (200 mL) was added dropwise to the reaction mixture, followed by supplementation with water (200 mL) and stirring to separate the mixture into layers. The organic layer was washed with 0.5N hydrochloric acid (200 mL) and washed with water. Methanol (400 mL) and p-TSA·H$_2$O (4.7 g, 0.1 eq) were added thereto, and the mixture was stirred for 3 hours. Sodium hydrogen carbonate (5.22 g) was added, and the mixture was stirred for 10 minutes, followed by concentration by drying. Dichloromethane (200 mL) and water (100 mL) were added thereto to separate the mixture into layers. The organic layer was washed with a saturated sodium chloride solution (100 mL), dried over anhydrous sodium sulfate, and dried by concentration, thereby obtaining a 3-(15-hydroxypentadecyl)-2,4,4-trimethylcyclohex-2-en-1-one crude product (103.9 g, 120%). The content (HPLC external standard method) was 68.5%.

Preparation of Compound II

Example 18

[3-(15-hydroxypentadecyl)-2,4,4-trimethylcyclohex-2-ene]-aminoformylhydrazone 3-(15-hydroxypentadecyl)-2,4,4-trimethylcyclohex-2-en-1-one crude product III (obtained in Example 17, content: 68.5%) (10.4 g, 1 eq) was dissolved in ethanol (70 mL), and water (35 mL) was added thereto. Semicarbazide hydrochloride (3.98 g, 1.5 eq) was added, and anhydrous sodium acetate (3.9 g, 2 eq) was added, followed by stirring to completely dissolve them. The solution was then heated under reflux overnight with stirring to precipitate solids. TLC confirmed that the starting materials completely reacted. The solvent was removed by concentration, and water (50 mL) was added thereto, followed by trituration at room temperature for 30 minutes. The resultant was filtered, and washed with water, followed by trituration the solids with acetonitrile (50 mL) for 30 minutes. The resultant was then filtered and dried by heating, thereby obtaining 8.14 g of 3-(15-hydroxypentadecyl)-2,4,4-trimethylcyclohex-2-ene-1-aminoformylhydrazone as whitish solids (calculated based on compound IV-1, three-step yield: 81.2%). The melting point was 150 to 152° C.

$^1$H NMR (400 MHz, DMSO-d$_6$) δ 8.98 (s, 1H), 6.24 (s, 2H), 4.32 (s, 1H), 3.35 (d, 5H, J=13.8 Hz), 2.35 (d, 1H, J=7.3 Hz), 2.11 (s, 2H), 1.79 (s, 2H), 1.51 (s, 1H), 1.39 (s, 2H), 1.33 (s, 8H), 1.25 (s, 16H), 1.02 (s, 6H).

|  |  | Impurities Content | | |
|---|---|---|---|---|
| Wavelength | Target Compound II-1 Purity | Hydrazone impurities resulting from non-desorption of hydroxy-protecting groups | Starting Materials | Other Individual Impurities |
| 210 nm | 98.99% | 0.79% | 0.09% | Less than 0.15% |
| 254 nm | 99.07% | 0.68% | 0.17% | Less than 0.15% |

Example 19

[3-(15-hydroxypentadecyl)-2,4,4-trimethylcyclohex-2-ene]-4-methylbenzolsulfonyl hydrazone

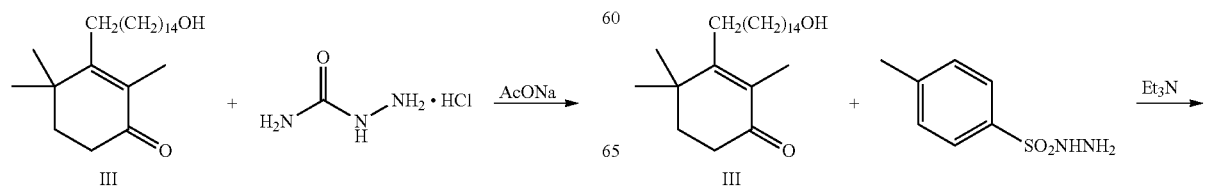

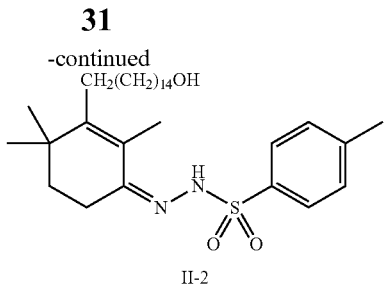

II-2

3-(15-hydroxypentadecyl)-2,4,4-trimethylcyclohex-2-en-1-one crude product III (5 g, 1 eq) (obtained in Example 15, content: 70.2%) was dissolved in ethanol (50 mL), and water (25 mL) was added thereto p-Toluenesulfonyl hydrazone (6.38 g, 2.5 eq) was added, and triethylamine (2.78 g, 2 eq) was added, followed by stirring to completely dissolve them. The solution was heated until the internal temperature reached 60 to 70° C. and stirred overnight to precipitate solids. TLC confirmed that the starting materials completely reacted. The solvent was removed by concentration, and water (50 mL) was added thereto, followed by trituration at room temperature for 30 minutes. The resultant was filtered, and washed with water, followed by triturating the solids with acetonitrile (50 mL) for 30 minutes. The resultant was filtered and dried by heating, thereby obtaining 3.56 g of 3-(15-hydroxypentadecyl)-2,4,4-trimethylcyclohex-2-ene-1-aminoformylhydrazone as whitish solids (calculated based on compound IV-1, three-step yield: 81.2%).

$^1$H NMR (400 MHz, CDCl$_3$) δ 7.82-7.80 (m, 2H), 7.33-7.31 (m, 2H), 4.30 (t, 2H, J=7.0 Hz), 2.42 (s, 2H), 2.30-2.22 (m, 2H), 2.11 (t, J=7.1 Hz, 2H), 1.89 (s, 2H), 1.49 (dt, J=14.1, 7.0 Hz, 4H), 1.42-1.22 (m, 25H), 1.02 (s, 6H).

| Wave-length | Target Compound II-2 Purity | Hydrazone impurities resulting from non-desorption of hydroxy-protecting groups | Starting Materials | Other Individual Impurities |
|---|---|---|---|---|
| 210 nm | 98.43% | 1.34% | 0.08% | Less than 0.15% |
| 254 nm | 98.64% | 1.05% | 0.21% | Less than 0.15% |

Preparation of Compound I

Example 20

3-(15-hydroxypentadecyl)-2,4,4-trimethylcyclohex-2-en-1-one

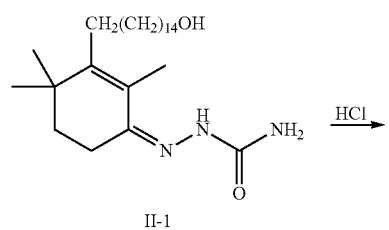

II-1

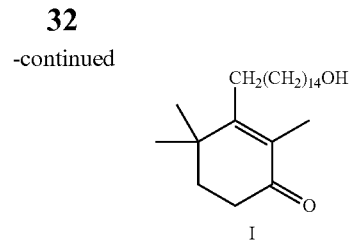

I

[3-(15-hydroxypentadecyl)-2,4,4-trimethylcyclohex-2-ene]-aminoformylhydrazone II-1 (100 g) was added to THF (200 mL) and 3N hydrochloric acid (500 mL), and protected by nitrogen gas. The solution was heated to 55 to 60° C. and stirred for 2 hours to separate it into layers to form two phases, followed by cooling to 45° C., thereby separating it into layers. The aqueous layer was separated and removed, and the organic layer was dispersed in n-heptane (200 mL), followed by sequential washing with a saturated sodium hydrogen carbonate solution (200 mL) and a saturated sodium chloride solution (100 mL). The resultant was dried over anhydrous sodium sulfate, and activated carbon (5 g) was added thereto, followed by stirring for 20 minutes. The mixture was filtered and dried by concentration n-heptane (1000 mL) was added to dissolve it, and the temperature was decreased to 0 to 10° C. with stirring, followed by stirring for 2 hours. The resultant was filtered, and the solids were dried under reduced pressure, thereby obtaining 3-(15-hydroxypentadecyl)-2,4,4-trimethylcyclohex-2-en-1-one (79 g, 91%) as whitish solids or a pale-color oil. The melting point was 36 to 38° C.

$^1$H NMR (400 MHz, CDCl$_3$): δ 3.61 (t, 2H, J=6.8 Hz), 2.43 (t, 2H, J=9.6 Hz), 2.13-2.17 (m, 2H), 1.77-1.80 (m, 3H), 1.73 (s, 3H), 1.49-1.55 (m, 2H), 1.21-1.42 (m, 24H), 1.13 (s, 6H). HPLC: 99.98%, individual impurities <0.05% (210 nm, 254 nm).

Example 21

3-(15-hydroxypentadecyl)-2,4,4-trimethylcyclohex-2-en-1-one

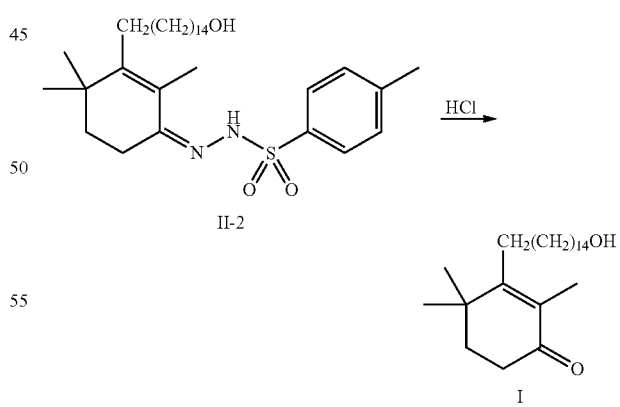

[3-(15-hydroxypentadecyl)-2,4,4-trimethylcyclohexyl-2-ene]-methylbenzolsulfonyl hydrazone II-2 (50 g) was added to THF (100 mL) and 3N hydrochloric acid (250 mL), and protected by nitrogen gas. The solution was heated to 55 to 60° C. and stirred for 2 hours to separate it into layers to form two phases, followed by cooling to 45° C., thereby separating it into layers. The aqueous layer was separated and removed, and the organic layer was dispersed in n-heptane (100 mL), followed by sequential washing with saturated sodium hydrogen carbonate (100 mL) and a saturated sodium chloride solution (50 mL). The resultant was dried over anhydrous sodium sulfate, and activated carbon (5 g) was added thereto, followed by stirring for 20 minutes. The mixture was filtered and dried by concentration n-heptane (1000 mL) was added to dissolve it, and the temperature was decreased to 0 to 10° C. with stirring, followed by stirring for 2 hours. The resultant was filtered, and the solids were dried under reduced pressure, thereby obtaining, 3-(15-hydroxypentadecyl)-2,4,4-trimethylcyclohex-2-en-1-one (27.4 g, 80%) as whitish solids or a pale-color oil.

$^1$H NMR (400 MHz, CDCl$_3$): δ 3.61 (t, 2H, J=6.8 Hz), 2.43 (t, 2H, J=9.6 Hz), 2.13-2.17 (m, 2H), 1.77-1.80 (m, 3H), 1.73 (s, 3H), 1.49-1.55 (m, 2H), 1.21-1.42 (m, 24H), 1.13 (s, 6H). HPLC: 99.95%, individual impurities <0.05% (210 nm, 254 nm).

The invention claimed is:

1. A method for producing a high-purity cyclohexenone long-chain alcohol represented by formula I, as shown in the following reaction scheme:

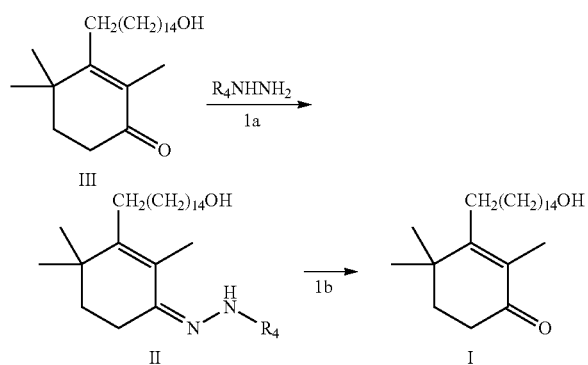

wherein
R$_4$ represents

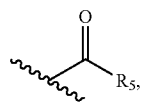

and R$_5$ represents amino;
the method comprising the steps of
(1a) subjecting a cyclohexenone long-chain alcohol crude product III and a hydrazine derivative R$_4$NHNH$_2$ to a condensation reaction to obtain a compound II, and
(1b) hydrolyzing the compound II in the presence of an acidic substance to obtain the high-purity compound I.

2. The production method according to claim 1, wherein the high-purity cyclohexenone long-chain alcohol represented by formula I has a purity by HPLC of more than 95%.

3. The production method according to claim 1, wherein step (1a) is performed in the presence of an acid, an alkali, or a desiccant;
the alkali is one member or two or more members selected from the group consisting of sodium alkoxide, potassium alkoxide, magnesium oxide, calcium oxide, sodium carbonate, potassium carbonate, lithium carbonate, cesium carbonate, calcium carbonate, sodium acetate, potassium acetate, lithium acetate, sodium benzoate, potassium benzoate, lithium benzoate, triethylamine, trimethylamine, diisopropylethylamine, 1,8-diazabicyclo[5.4.0]undec-7-ene, 1,5-diazabicyclo[4.3.0]non-5-ene, and triethylenediamine;
the acid is one member or two or more members selected from the group consisting of acetic acid, benzoic acid, hydrochloric acid, sulfuric acid, phosphoric acid, benzenesulfonic acid, p-toluenesulfonic acid, camphorsulfonic acid, boron trifluoride ethyl ether, scandium trifluoromethanesulfonate, indium trifluoromethanesulfonate, and bismuth trifluoromethanesulfonate; and
the desiccant is one member or two or more members selected from the group consisting of a molecular sieve, magnesium sulfate, sodium sulfate, and calcium hydride.

4. The production method according to claim 1, wherein the molar ratio of the hydrazine derivative R$_4$NHNH$_2$ to the cyclohexenone long-chain alcohol crude product III is 0.8:1 to 3:1.

5. The production method according to claim 1, wherein the condensation reaction is performed in a solvent;
the solvent is one member or two or more members selected from the group consisting of methanol, ethanol, isopropanol, n-butanol, tert-butanol, tert-pentanol, acetonitrile, tetrahydrofuran, methyl tert-butyl ether, isopropyl ether, dioxane, acetone, 2-butanone, ethyl acetate, isobutyl acetate, toluene, xylene, chlorobenzene, benzene, N,N-dimethylacetamide, N,N-dimethylformamide, N,N-diethylformamide, N-methylpyrrolidone, dichloromethane, 1,2-dichloroethane, chloroform, n-hexane, n-heptane, cyclohexane, and water;
the temperature of the condensation reaction is 0 to 149° C.; and
the reaction time of the condensation reaction is 0.5 to 24 hours.

6. The production method according to claim 1, wherein the acidic substance recited in step (1b) is one member or two or more members selected from the group consisting of an organic acid, an inorganic acid, a Lewis acid, an acid salt, and other acidic substance;
the inorganic acid is selected from the group consisting of sulfuric acid, hydrochloric acid, phosphoric acid, polyphosphoric acid, and phosphotungstic acid;
the organic acid is selected from the group consisting of formic acid, acetic acid, propionic acid, oxalic acid, fumaric acid, maleic acid, trifluoroacetic acid, methanesulfonic acid, benzenesulfonic acid, p-toluenesulfonic acid, camphorsulfonic acid, and trifluoromethanesulfonic acid;
the Lewis acid is selected from the group consisting of boron trifluoride ethyl ether, aluminum trichloride, iron trichloride, bismuth trifluoromethanesulfonate, and scandium trifluoromethanesulfonate;
the acid salt is selected from the group consisting of sodium hydrogensulfate, ammonium hydrogensulfate, magnesium hydrogensulfate, pyridinium p-toluenesulfonate, triethylamine hydrochloride, and pyridine hydrochloride;
the other acidic substance is silica gel or acidic resin; and
the molar ratio of the added amount of the compound II to the added amount of the acidic substance is 1:0.2 to 1:10.

7. The production method according to claim 1, wherein the hydrolysis reaction is performed in a solvent;
the solvent is one member or two or more members selected from the group consisting of benzene, toluene, chlorobenzene, xylene, acetonitrile, 2-butanone, acetone, 1,2-dimethyl-2-imidazolone, dimethyl sulfoxide, dimethyl sulfone, sulfolane, hexamethylphosphoric triamide, N,N-dimethylformamide, N,N-dimethylacetamide, N,N-diethylformamide, N-methylpyrrolidone, methanol, ethanol, isopropanol, n-butanol, ethylene glycol, polyethylene glycol, dioxane, methyl tert-butyl ether, isopropyl ether, tetrahydrofuran, n-hexane, cyclohexane, dichloromethane, 1,2-dichloroethane, chloroform, and water;
the reaction temperature of the hydrolysis reaction is 20 to 139° C., and the reaction time of the hydrolysis reaction is 0.5 to 24 hours.

8. The production method according to claim 1, wherein the cyclohexenone long-chain alcohol crude product III is produced as shown in the following reaction scheme:

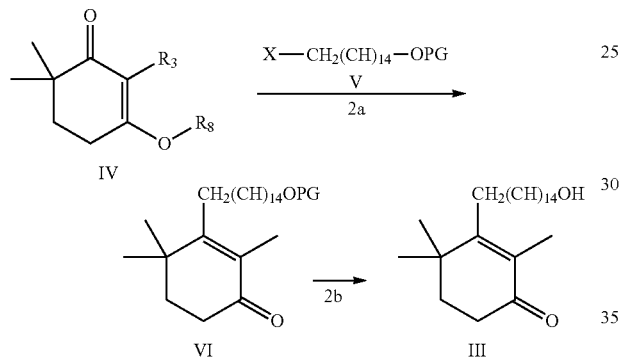

wherein X represents halogen, $R_8$ represents $C_{1-7}$ alkyl, $C_{6-14}$ aryl, or

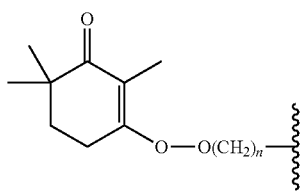

wherein n represents 1 to 12,
PG represents

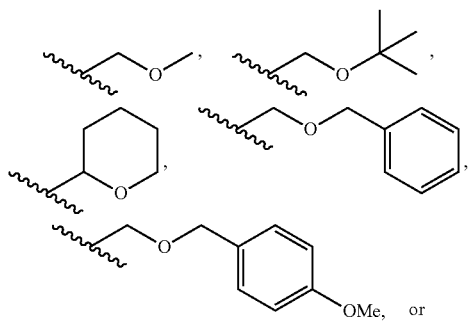

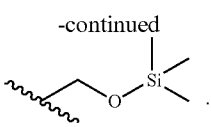

the method comprising the steps of
(2a) subjecting a compound IV and a compound V to a metal-mediated Barbier reaction to generate a compound VI, and
(2b) subjecting the compound VI to a deprotection reaction in the presence of an acidic substance to remove a protective group, thereby obtaining the cyclohexenone long-chain alcohol crude product III.

9. The production method according to claim 8, wherein in step (2a),
the metal is selected from the group consisting of lithium, sodium, strontium, magnesium, and zinc,
the molar ratio of the metal to the compound IV is 1:1 to 12:1, and
the molar ratio of the compound V to the compound IV is 0.6:1 to 6:1.

10. The production method according to claim 8, wherein
the Barbier reaction is performed in the presence or absence of a catalyst,
the catalyst is one member or two or more members selected from the group consisting of tetramethylethylenediamine and hexamethylphosphoric triamide,
the molar ratio of the catalyst to the compound IV is 0.2:1 to 2:1,
the Barbier reaction is performed in a suitable solvent,
the solvent is one member or two or more members selected from the group consisting of benzene, toluene, chlorobenzene, xylene, tetrahydrofuran, methyltetrahydrofuran, dioxane, methyl tert-butyl ether, n-hexane, n-heptane, cyclohexane, acetonitrile, hexamethylphosphoric triamide, and sulfolane,
the temperature of the Barbier reaction is −20 to 100° C., and
the reaction time of the Barbier reaction is 1 to 36 hours.

11. The production method according to claim 8, wherein in step (2b),
the acidic substance is one member or two or more members of methanesulfonic acid, benzenesulfonic acid, p-toluenesulfonic acid, camphorsulfonic acid, pyridinium p-toluenesulfonate, triethylamine hydrochloride, hydrochloric acid, sulfuric acid, phosphoric acid, sodium hydrogensulfate, magnesium hydrogensulfate, an acidic molecular sieve, acidic resin, acetic acid, trifluoroacetic acid, trifluoromethanesulfonic acid, iron trichloride, boron trifluoride ethyl ether, chlorotrimethylsilane, and acetyl chloride,
the molar ratio of the acidic substance to the compound VI is 0.02:1 to 1:1,
the deprotection reaction is performed in a suitable solvent, and the solvent is one member or two or more members of methanol, ethanol, isopropanol, n-butanol, tert-butanol, tert-pentanol, acetonitrile, tetrahydrofuran, methyl tert-butyl ether, isopropyl ether, dioxane, acetone, 2-butanone, ethyl acetate, isobutyl acetate, toluene, xylene, chlorobenzene, benzene, N,N-dimethylacetamide, N,N-dimethylformamide, N,N-diethylformamide, N-methylpyrrolidone, dichloromethane, 1,2-dichloroethane, chloroform, n-hexane, n-heptane, cyclohexane, and water, the reaction temperature of the deprotection reaction is −20 to 100° C., and the reaction time of the deprotection reaction is 0.1 to 10 hours.

12. The production method according to claim 8, wherein step (2a) and step (2b) may be separately performed stepwise, or may be performed by a one-pot reaction method.

13. The production method according to claim 1, wherein the cyclohexenone long-chain alcohol crude product III is as shown in the following reaction scheme:

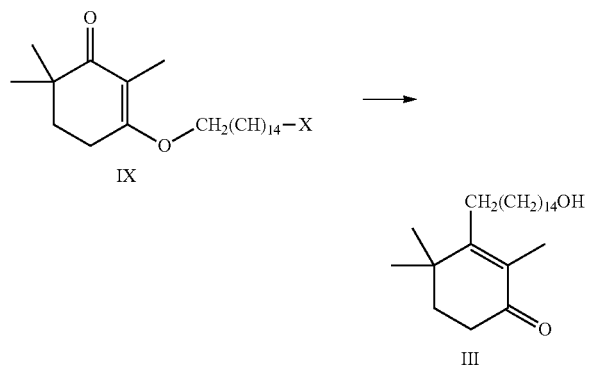

wherein X represents halogen and a compound IX is subjected to a metal-mediated intermolecular Barbier reaction to obtain the cyclohexenone long-chain alcohol crude product III.

14. The production method according to claim 13, wherein
the metal is lithium, sodium, strontium, magnesium, or zinc, and
the molar ratio of the metal to the compound IX is 1:1 to 12:1.

15. The production method according to claim 13, wherein
the Barbier reaction is performed in the presence or absence of a catalyst,
the catalyst is one member or two or more members selected from the group consisting of tetramethylethylenediamine and hexamethylphosphoric triamide,
the molar ratio of the catalyst to the compound IX is 0.2 to 2:1,
the Barbier reaction is performed in a suitable solvent, and
the solvent is one member or two or more members selected from the group consisting of benzene, toluene, chlorobenzene, xylene, tetrahydrofuran, methyltetrahydrofuran, dioxane, methyl tert-butyl ether, n-hexane, n-heptane, cyclohexane, acetonitrile, hexamethylphosphoric triamide, and sulfolane,
the reaction temperature of the Barbier reaction is −20 to 100° C., and
the reaction time of the Barbier reaction is 1 to 36 hours.

* * * * *